(12) United States Patent
Campbell et al.

(10) Patent No.: US 11,365,413 B2
(45) Date of Patent: Jun. 21, 2022

(54) INHIBITION OF POLY(A) BINDING PROTEIN AND THE TREATMENT OF PAIN

(71) Applicant: Board of Regents, The University of Texas System, Austin, TX (US)

(72) Inventors: Zachary T. Campbell, Plano, TX (US); Theodore J. Price, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 183 days.

(21) Appl. No.: 16/547,882

(22) Filed: Aug. 22, 2019

(65) Prior Publication Data

US 2020/0087662 A1    Mar. 19, 2020

Related U.S. Application Data

(60) Provisional application No. 62/721,088, filed on Aug. 22, 2018.

(51) Int. Cl.
| | |
|---|---|
| *C12N 15/113* | (2010.01) |
| *A61K 31/7125* | (2006.01) |
| *A61K 9/70* | (2006.01) |
| *A61P 29/00* | (2006.01) |
| *A61K 9/00* | (2006.01) |
| *A61K 45/06* | (2006.01) |

(52) U.S. Cl.
CPC .......... *C12N 15/113* (2013.01); *A61K 9/0014* (2013.01); *A61K 9/7023* (2013.01); *A61K 31/7125* (2013.01); *A61P 29/00* (2018.01); *A61K 45/06* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| | | | | |
|---|---|---|---|---|
| 6,211,162 B1* | 4/2001 | Dale | ...................... | A61K 8/606 |
| | | | | 514/44 R |
| 2010/0113565 A1* | 5/2010 | Gorden | .................. | A61K 39/39 |
| | | | | 514/44 R |
| 2017/0327825 A1 | 11/2017 | Karni | | |

OTHER PUBLICATIONS

Taherpour et al. RSC Advances 2015, vol. 5, pp. 10837-10844.*
Barragán-Iglesias et al., Inhibition of Poly(A)-binding protein with a synthetic RNA mimic reduces pain sensitization in mice; *Nature Communications* (2018) 9:10; DOI: 10.1038/s41467-017-02449-5 l.
Campbell et al., A protein-RNA specificity code enables targeted activation of an endogenous human transcript. Nat. Struct. Mol. Biol. 21, 732-738 (2014).
Campbell et al., Cooperativity in RNA-protein interactions: global analysis of RNA binding specificity. Cell Rep. 1, 570-581 (2012).
Campbell et al., Identification of a conserved interface between PUF and CPEB proteins. J. Biol. Chem. 287, 18854-18862 (2012).
Campbell et al., Oligodeoxynucleoside phosphorothioate stability in subcellular extracts, culture media, sera and cerebrospinal fluid. J. Biochem. Biophys. Methods 20, 259-267 (1990).
Campbell, Z., (Aug. 2017) *Inhibition of Poly(A)-Binding Protein with an RNA mimic reduces pain sensitization in mice;* Public presentation at UT-Dallas.
de la Peña and Campbell, RNA-binding proteins as targets for pain therapeutics, Neurobiology of Pain, vol. 4, 2018, pp. 2-7, ISSN 2452-073X, https://doi.org/10.1016/j.ynpai.2018.01.003.
Denichenko et al., Specific inhibition of splicing factor activity by decoy RNA oligonucleotides; *Nat Commun* 10, 1590, doi:10.1038/s41467-019-09523-0 (2019).
Dias, N. & Stein, C. A. Antisense oligonucleotides: basic concepts and mechanisms. Mol. Cancer Ther. 1, 347-355 (2002).
Filipowicz, W., et al., Regulation of mRNA Translation and Stability by microRNAs, *Annual Review of Biochemistry*, vol. 79:351-379 (Volume publication date Jul. 7, 2010); https://doi.org/10.1146/annurev-biochem-060308-103103.
Gallie , The cap and poly(A) tail function synergistically to regulate mRNA translational efficiency; *Genes Dev.* 1991, 5:; Access the most recent version at doi:10.1101/gad.5.11.2108.
Gerhold et al., The star-nosed mole reveals clues to the molecular basis of mammalian touch. PLoS ONE 8, e55001 (2013).
Hernandez, F. J. et al. Degradation of nuclease-stabilized RNA oligonucleotides in Mycoplasma-contaminated cell culture media. Nucleic Acid Ther. 22, 58-68 (2012).
Khoutorsky et al., Translational control of nociception via 4E-binding protein 1. eLife 4, //doi.org/10.7554/eLife.12002 (2015).
Kini et al., Cytoplasmic poly(A) binding protein-1 binds to genomically encoded sequences within mammalian mRNAs. RNA 22, 61-74 (2016).
Kole et al., RNA therapeutics: beyond RNA interference and antisense oligonucleotides. Nat. Rev. Drug. Discov. 11, 125-140 (2012).
Mühlemann and Nicholson; Cutting the nonsense: the degradation of PTC-containing mRNAs. Biochem Soc Trans Dec. 1, 2010; 38 (6): 1615-1620. doi: https://doi.org/10.1042/BST0381615.
Obara et al., Axonal protein synthesis: a potential target for pain relief?; *Current Opinion in Pharmacology* 2012, 12:42-48.
Orellana et al., Sci. Transl. Med. 9, eaam9327 (2017).
Smith RW. et al., Poly(A)-binding proteins and mRNA localization: who rules the roost?.; Biochem Soc Trans Dec. 1, 2015; 43 (6): 1277-1284. doi: https://doi.org/10.1042/BST20150171.

(Continued)

*Primary Examiner* — Tracy Vivlemore
(74) *Attorney, Agent, or Firm* — Parker Highlander PLLC

(57) ABSTRACT

The present disclosure describes chemically-stabilized RNA substrates that hybridize to poly-A binding protein (PABP) with high specificity in vitro, as well as their use in impairs nascent translation in a PABP-dependent mechanism in cells, thereby treating pain.

22 Claims, 10 Drawing Sheets
(10 of 10 Drawing Sheet(s) Filed in Color)
Specification includes a Sequence Listing.

(56) References Cited

OTHER PUBLICATIONS

Tolino, M., et al.; RNA-binding proteins involved in RNA localization and their implications in neuronal diseases; *European Journal of Neuroscience,* vol. 35, pp. 1818-1836, 2012 doi: 10.1111/j.,1460-9568.2012.08160.x.

Tritschler, F., Huntzinger, E. & Izaurralde, E., Role of GW182 proteins and PABPC1 in the miRNA pathway: a sense of déjà vu. *Nat Rev Mol Cell Biol* 11, 379-384 (2010). https://doi.org/10.1038/nrm2885.

Weidmann et al., *Drosophila* nanos acts as a molecular clamp that modulates the RNA-binding and repression activities of Pumilio. eLife 5, https//doi.org/10.7554/eLife.17096 (2016).

Wu C. et al., Cordycepin activates AMP-activated protein kinase (AMPK) via interaction with the cl subunit, J. Cell. Mol. Med. 18: 293-304, 2014.

\* cited by examiner

SEQUENCE LISTING

```
<160> NUMBER OF SEQ ID NOS: 5

<210> SEQ ID NO 1
<211> LENGTH: 12
<212> TYPE: RNA
<213> ORGANISM: Artificial sequence
<220> FEATURE:
<223> OTHER INFORMATION: Synthetic oligo
<220> FEATURE:
<221> NAME/KEY: modified_base
<222> LOCATION: (1)..(12)
<223> OTHER INFORMATION: 2'O-Methyladenine
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage

<400> SEQUENCE: 1
aaaaaaaaaa aa                                                         12

<210> SEQ ID NO 2
<211> LENGTH: 15
<212> TYPE: RNA
<213> ORGANISM: Artificial sequence
<220> FEATURE:
<223> OTHER INFORMATION: Synthetic oligo

<400> SEQUENCE: 2
aaaaaaaaaa aaaaa                                                      15

<210> SEQ ID NO 3
<211> LENGTH: 12
<212> TYPE: RNA
```

```
<213> ORGANISM: Artificial sequence
<220> FEATURE:
<223> OTHER INFORMATION: Synthetic oligo
<220> FEATURE:
<221> NAME/KEY: misc_feature
<222> LOCATION: (1)..(2)
<223> OTHER INFORMATION: phosphorothioate linkages
<220> FEATURE:
<221> NAME/KEY: misc_feature
<222> LOCATION: (11)..(12)
<223> OTHER INFORMATION: phosphorothioate linkages

<400> SEQUENCE: 3
aaaaaaaaaa aa                                                            12

<210> SEQ ID NO 4
<211> LENGTH: 12
<212> TYPE: RNA
<213> ORGANISM: Artificial sequence
<220> FEATURE:
<223> OTHER INFORMATION: Synthetic oligo
<220> FEATURE:
<221> NAME/KEY: misc_feature
<222> LOCATION: (1)..(2)
<223> OTHER INFORMATION: phosphorothioate linkages
<220> FEATURE:
<221> NAME/KEY: misc_feature
<222> LOCATION: (11)..(12)
<223> OTHER INFORMATION: phosphorothioate linkages

<400> SEQUENCE: 4
uaacaaaaua au                                                            12

<210> SEQ ID NO 5
<211> LENGTH: 10
<212> TYPE: DNA
<213> ORGANISM: Artificial sequence
<220> FEATURE:
<223> OTHER INFORMATION: Synthetic oligo

<400> SEQUENCE: 5
aaaaaaaaaa                                                               10
```

INHIBITION OF POLY(A) BINDING PROTEIN AND THE TREATMENT OF PAIN

PRIORITY CLAIM

This application claims benefit of priority to U.S. Provisional Application Ser. No. 62/721,088, filed Aug. 22, 2018, the entire contents of which are hereby incorporated by reference.

STATEMENT OF FEDERAL GRANT SUPPORT

This invention was made with Government support under grant nos. R01 NS065926 and R01 NS100788 awarded by the National Institutes of Health. The Government has certain rights in this invention.

INCORPORATION OF SEQUENCE LISTING

The sequence listing that is contained in the file named "UTSFP0141US_ST25.txt", which is 2 KB (as measured in Microsoft Windows®) and was created on Aug. 22, 2019, is filed herewith by electronic submission and is incorporated by reference herein.

BACKGROUND

1. Field

The present disclosure relates to the fields of cell biology, molecular biology, protein biology and neurology. More specifically, it describes the inhibition of poly(A) binding proteins, such as for treatment of pain.

2. Description of Related Art

Post-transcriptional gene control is a dominant theme in neuronal plasticity (Wang & Tiedge, 2004; Costa-Mattioli et al., 2009). Messenger RNA (mRNA) possess two distinct structural features on opposing ends: a cap and a Poly(A) tail. Each structure serves as a molecular scaffold that nucleates the formation of dynamic multiprotein regulatory complexes (Eckmann et al., 2011; Sonenberg & Hinnebusch, 2009; Gallie, 1998). These large assemblies enable signal-dependent control of protein synthesis. The cap-binding complex, consisting of eIF4F proteins, has emerged as a key player in pain sensitization (Moy et al., 2017; Khoutorsky et al., 2015; Melemedjian et al., 2010). Pain can be triggered by inflammation, nerve injury, and production of inflammatory cytokines (e.g., nerve growth factor (NGF) and interleukin 6 (IL-6)). NGF and IL-6 rapidly stimulate cap-dependent translation in nociceptors, resulting in long-term changes in excitability (Melemedjian et al., 2010). Far less is known regarding the regulatory impact of pro-inflammatory signals on regulation that occurs on the 3' end.

Regulated cytoplasmic polyadenylation serves crucial roles in the developing nervous system and in the adult nervous system (Sonenberg & Hinnebusch, 2007). Moreover, synaptic plasticity can result in stimulation of factors that trigger addition of adenosines onto the 3' end of mRNA (Wu et al., 1998; Kundel et al., 2009; Wells et al., 2001). The direct consequence of Poly(A) extension is increased binding of Poly(A)-binding proteins (PABPs) (Gorgoni & Gray, 2004). PABPs are master regulators of mRNA stability; their association with the Poly(A) tail protects the 3' end from deadenylation and subsequent decay (Morales et al., 1997; Couttet et al., 1997; Burgess & Gray, 2010). PABPs promote translation initiation through simultaneous associations with the Poly(A) tail and translation factors associated with the 5' 7-methyl guanosine cap (Gorgoni & Gray, 2004). The interaction between eIF4G and PABP is essential for circularizing mRNA prior to eIF3-mediated recruitment of the 40S ribosomal subunit. RNA circularization is dictated by availability of PABPs, which is in turn controlled by the length of the Poly(A) tail.

Despite recent evidence for PABP function in the central nervous system, little is known regarding the role of PABPs in induced plasticity (Khoutorsky et al., 2015). For many RNA-binding proteins, specificity is well-established (Ray et al., 2013). In principle, this information provides a means to generate RNA-based competitive inhibitors. However, a major complication of this approach is the ephemeral nature of RNA. RNA is rapidly degraded by exonucleolytic and endonucleolytic pathways. However, significant advances have been made in increasing RNA stability through the use of chemical modifications to the RNA 2' hydroxyl group and the phosphodiester linkage (Dias & Stein, 2002; Kole et al., 2012). These enhancements can increase RNA stability by an order of magnitude (Campbell et al., 1990).

SUMMARY

Thus, in accordance with the present disclosure, there is provided a compound comprising a chemically-stabilized RNA substrate that hybridizes to an RNA binding protein (RNA-BP) with high specificity in vitro and alters RNA processing, alters RNA stability and/or impairs nascent translation in RNA-BP-dependent mechanism in cells. The RNA-BP may be poly-A binding protein (PABP), eukaryotic translation initiation factor 4E (eIF4E), HuD or ELAV Like RNA Binding Protein 4 (Elav14), HuR or ELAV Like RNA Binding Protein 1 (Elav11), Cytoplasmic polyadenylation element binding protein (CPEB), or Fragile X mental retardation protein (FMRP). The compound may be 11-15 bases in length. The chemical stabilization may comprise either or both a phosphorothioate bond and/or a 2'O-Methyl modification. The chemically-stabilized RNA substrate may be represented by the formula:

$$[mA]^*[mA][mA][mA][mA][mA][mA][mA][mA][mA]$$
$$[mA]^*[mA] \qquad \text{(SEQ ID NO: 1)}$$

wherein each base is bracketed, * denotes a phosphorothioate bond, and m denotes 2'O-Methyl modification. The compound may further comprise a targeting agent linked to said chemically-stabilized RNA. A pharmaceutical composition comprising the compound as described above is also disclosed.

In another embodiment, there is provided a method of altering RNA processing, altering RNA stability and/or impairing nascent translation in a subject comprising administering to said subject a compound as described above, or a pharmaceutical composition comprising the compound. Administering may comprise oral, intravenous, intra-arterial administration or subcutaneous administration, such as by a transdermal patch. The subject may be a human or a non-human mammal. The method may comprise administering the compound a second time, such as in chronic administration.

The subject may suffer from pain and said administering treats said pain. Administering may comprise administering local or regional to a site of pain, such as by a transdermal patch. The method may further comprise administering to said subject one or more of an NSAID, an opiate, or a steroid. The pain may be neuropathic pain, such as peripheral neuropathic pain, or may be inflammatory pain, such as nociceptive pain. The pain may also be chronic pain or severe/acute pain.

In another embodiment, there is provided a method of reducing opioid tolerance in a subject suffering from pain and receiving opiate therapy comprising co-administering to the subject an amount of compound or pharmaceutical composition as described above, sufficient to reduce opioid tolerance. The opioid may be morphine, oxycodone, or fentanyl. The pain may be the result of an injury, such as a penetration wound, a burn, frostbite or a fracture, or is the result of a disease, such as diabetes, postsurgical pain, bone cancer pain, spinal nerve injuries, multiple sclerosis, arthritis, an autoimmune disease, or an infection. The subject may be a human or non-human mammal. The pain may be chronic pain or acute pain. The opiate and the compound may be are delivered at the same time. The opiate and the compound may be co-formulated. The opiate and the compound may be formulated separately. The opiate and the compound may be delivered at distinct times, such as where the opioid is delivered before the compound, or where the opioid is delivered after the compound. The opiate and the compound may be delivered in alternating administrations. The compound and the opiate may be delivered over a period of one week, two weeks, three weeks, four weeks, one month, two months, three months, four months, five months, six months, seven months, eight months, nine months, ten months, eleven months, one year, two years or three years. The opiate and/or the compound may be delivered by continuous infusion, such as provided by an implanted pump. The opiate and/or the compound may be delivered via a transdermal patch. The opiate and/or the compound may be delivered intravenously or intra-arterially. Administering may comprise administering local or regional to a site of pain.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

(FIG. 1A) The SEQRS strategy begins with in vitro transcription of a DNA library containing a T7 primer (light blue), two constant regions (Primers a and b, dark blue), and a randomized 20-mer (purple). Following in vitro transcription, the library was incubated with PABP immobilized onto magnetic resin (green). RNA-protein complexes were isolated through wash steps and the bound RNAs were reverse transcribed. The T7 promoter was reattached through incorporation into a PCR primer and the process was repeated for five rounds prior to Illumina high-throughput sequencing. (FIG. 1B) Reproducibility of SEQRS. The most abundant 120,000 sequences for SEQRS replicates have a Pearson's correlation coefficient of 0.7. The most enriched 10-mer sequence is an adenosine homopolymer and is indicated with an arrow (SEQ ID NO: 5). (FIG. 1C) Positions of the 50 most enriched 8-mer sequences from SEQRS for either PABP (green) or random sequences (purple) were calculated across known sites of PABP association outside of the Poly(A) tail in cells (Kini et al., 2016). Enrichment scores were calculated based on the Mann-Whitney U test. (FIG. 1D) The area under the receiver operator curve is 0.81. (FIG. 1E) The sequence logo based on the top 300 10-mer sequences following SEQRS. (SEQ ID NO: 5)

(FIG. 2A) The experimental approach for generation of PABPdepleted extracts consisted of immobilization of the PABP-interacting protein (PAIP, purple) onto resin (blue). Extracts containing PABP (green) were allowed to incubate and were aspirated resulting in loss of PABP. Cy3-labeled SPOT-ONs were added to total protein lysates and analyzed by electrophoretic mobility shift assay (EMSA). (FIG. 2B) EMSA assays. SPOT-ONs were incubated with either total protein lysate or PAIP-treated lysate and incubated at 0° C. for 40 min prior to separation by non-denaturing electrophoresis. The position of free probe and a single population of protein/RNA complex is indicated. This population is only observed in the Poly(A) SPOT-ON sample and is sensitive to PAIP depletion. The scramble SPOT-ON failed to shift a single population of proteins. (FIG. 2C) Pull-down experiments were conducted from lysates as prepared in FIG. 2B, but the SPOT-ON was generated with a biotin tag. Immunostaining is shown for either PABP or actin as a negative control. The Poly(A) SPOT-ON specifically associated with PABP in PABP containing lysates. (FIG. 2D) Equilibrium dissociation constants were determined by florescence anisotropy measurements of either unmodified adenosine dodecamer (blue) or the Poly(A) SPOT-ON (green). A modified version of the Michaelis-Menten equation was utilized to determine the equilibrium dissociation constants of either 261±54 or 301±41 µM for the 12 base unmodified or Poly(A) SPOT-ON RNAs, respectively. (FIG. 2E) Stability measurements of Cy3-labeled Poly(A) (green) or scrambled (purple) SPOT-ONs were determined in 10% FBS incubated at 37° C. and compared to a non-stabilized Poly(A) RNA (blue). (FIG. 2F) Quantification of FIG. 2E, percentage remaining is based on the initial intensity of RNA at time zero. n=3. Data are plotted as mean±s.e.m. (FIG. 2G) Cellular uptake of SPOT-ONs was determined based on imaging of U2OS cells for the Poly(A) and scrambled SPOT-ONs over time. n=6. Data are plotted as mean±s.e.m. (FIG. 2H) Sample data are shown for the Poly(A) SPOT-ON at time zero and after 3 h.

(FIG. 3A) SUnSET measurements in U2OS cells were conducted in the absence of puromycin to determine background levels of signal. Puromycin staining (green), phallodin (red), DNA (blue), and the merge between channels are arranged from top to bottom. As a positive control, puromycin and vehicle were used to determine the upper limit of translation. Both homoharringtonine (HHT) and the Poly(A) SPOT-ON robustly decrease protein synthesis, whereas the scrambled SPOT-ON failed to do so. (FIG. 3B) Quantification of FIG. 3A, empty boxes indicate no puromycin control, pink boxes are the positive control, blue boxed are homoharringtonine, green boxes are the Poly(A) SPOT-ON, and purple boxes are the scramble control. n=15. (FIG. 3C) PABP overexpression rescues decreased protein synthesis caused by the Poly(A) SPOT-ON. Drug treatments consisted of either vehicle or SPOT-ON in the presence of an empty vector or overexpressed PABP. The amount of vector is indicated above the row of images. Markers are arranged as in FIG. 3A. (FIG. 3D) Quantification of FIG. 3C. n=6. Columns represent measurements in the same manner as in b. *$P<0.05$, **$P<0.01$, significantly different from vehicle+puro group analyzed by one-way ANOVA followed by Bonferroni post hoc test. For all graphs shown in the figure, data are plotted as mean±s.d.

(FIG. 4A) In the first series of experiments, test compounds (e.g., hippuristanol) are added to cells and allowed to incubate prior to blockade of elongation with emetine. After 5 min puromycin is incorporated for a brief period of time. A predicted outcome of this experiment is that the ribosomes are susceptible to effects on initiation. (FIG. 4B) In a second series of experiments, elongation is blocked prior to initiation. Ribosomes are predicted to be insensitive to initiation inhibitors owing to prior arrest at a subsequent phase of translation (elongation). (FIGS. 4C-D) Order of addition is indicated for either vehicle, hippuristanol, SPOT-ON RNAs, emetine, or puromycin. All samples receive emetine at the indicated time points (a, b). As before, staining is shown from top to bottom for puromycin (green), phallodin (red), DNA (blue), or a merge. (FIG. 4E) Quantification of FIG. 4C, empty boxes indicate no puromycin control, pink boxes are the positive control, blue boxes are hippuristanol, green boxes are the Poly (A) SPOT-ON, and purple boxes are the scramble control. Both hippuristanol and the Poly(A) SPOT-ON possess defective translation, whereas the scramble SPOT-ON does not. n=6. (FIG. 4F) Quantification of FIG. 4D, where addition of emetine prior to test compounds fails to reveal significant differences for any of the test compounds. Columns represent measurements in the same manner as in FIG. 4E. n=6. *$P<0.05$, **$P<0.01$, significantly different from vehicle+emetine+puro group analyzed by one-way ANOVA followed by Bonferroni post hoc test. For all graphs shown in the figure, data are plotted as mean±s.d.

(FIG. 5A) Scramble SPOT-ON and (FIG. 5B) Poly(A) SPOT-ONs are taken up by DRG neurons and are localized into their axons after a 3-h period. (FIG. 5C) Quantification of SPOT-ONs uptake in DRG neurons from time zero to 6 h. n=6. Data are plotted as mean±s.e.m.

(FIG. 6A) Cultured DRG neurons are incubated with SPOT-ONs (10 µM) or homoharrintonine (50 µM) for 3 h prior to addition of puromycin (1 µM) for an additional 15 min. Incubation with Poly(A) SPOT-ON, but not scrambled SPOT-ON or vehicle, significantly reduces nascent protein synthesis in DRG neurons. Staining is shown from top to bottom for puromycin (green), peripherin (red), or a merge. (FIG. 6B) Quantification of a. n=6. *$P<0.05$, **$P<0.01$, significantly different from vehicle+puro group analyzed by oneway ANOVA followed by Bonferroni post hoc test. (FIG. 6C) Cultured DRG neurons are incubated with vehicle, SPOT-ONs, or hippuristanol for 3 h followed by emetine incubation (200 µM) for 5 min and puromycin (100 µM) for an additional 5 min. Incubation with Poly(A) SPOT-ON (10 µM), but not scrambled SPOT-ON or vehicle, significantly reduces proximal axonal translation (around 20-25 µM from the cell body) in peripherin-positive DRG axons. As in FIG. 6A, staining is shown from top to bottom for puromycin (green), peripherin (red), or a merge. (FIG. 6D) Representative images showing distal axonal ribopuromycylation (more than 25 µM from the cell body; randomly selected) in peripherin-positive DRG axons under identical conditions as described in FIG. 6C. (FIG. 6E) Quantification of images in FIG. 6B. n=20. *$P<0.05$, **$P<0.01$, significantly different from vehicle+E+P group analyzed by one-way ANOVA followed by Bonferroni post hoc test. (FIG. 6F) Quantification of images in FIG. 6D. n=9. *$P<0.05$, **$P<0.01$, significantly different from vehicle+E+P group analyzed by one-way ANOVA followed by Bonferroni post hoc test. For all graphs shown in the figure, data are plotted as mean±s.e.m.

(FIG. 7A) PABP (green) is highly expressed in cultured DRG neurons and their axons including growth cones and co-localizes with peripherin immunoreactivity, a marker for unmyelinated sensory neurons (red and merge). (FIG. 7B) PABP is broadly expressed in the majority of DRG neurons and co-localizes with peripherin and TRPV1, a nociceptive marker for both C and Aδ fibers. (FIG. 7C) PABP colocalizes with the neuronal marker NeuN and is also expressed in TRPV1-positive and IB4-positive pre-synaptic endings of DRG neurons in the spinal dorsal horn. PABP is also differentially expressed in microglia (CD11b+) and astrocytes (GFAP+) in the spinal dorsal horn. As shown in the figure, 18.6±1.9% of the PABP immunoreactive fibers co-localize with TRPV1, 11.3±1.2% with IB4, 29.1±1.7% with GFAP, and 14.8±2.2% with CD11b. n=5 slices from L4-L6 spinal dorsal horn. Data are expressed as mean±s.e.m. (FIG. 7D) PABP present in small-diameter sensory axons containing peripherin and in Schwann cells (MPz+) in the sciatic nerve.

FIGS. 8A-P. The Poly(A) SPOT-ON reduces pain sensitization in mice produced by intraplantar NGF or IL-6 administration and after plantar incision. (FIGS. 8A-B) Intraplantar injection with vehicle or scrambled SPOT-ON (0.3-1 µg) did not reduce NGF-induced mechanical hypersensitivity or priming produced by intraplantar injection with PGE2 (100 ng) at day 9 after surgery. (FIGS. 8A-D) d Intraplantar injection with Poly(A) SPOT-ON (1 µg) reduces NGF-induced mechanical hypersensitivity and blocked the development of PGE2-induced hyperalgesic priming. *$P<0.05$, **$P<0.01$, significantly different from NGF+vehicle group analyzed by two-way ANOVA followed by Bonferroni post hoc test. (FIGS. 8A-F) Intraplantar injection with vehicle or scrambled SPOT-ON (0.3-1 µg) did not reduce IL-6-induced mechanical hypersensitivity or priming produced by PGE2. (FIGS. 8G-H) h Intraplantar injection with Poly(A) SPOT-ON (1 µg) reduces IL-6-induced mechanical hypersensitivity and blocked the development of PGE2-induced hyperalgesic priming. *$P<0.05$, **$P<0.01$, significantly different from IL-6+vehicle group analyzed by two-way ANOVA followed by Bonferroni post hoc test. (FIGS. 8I-J) Following plantar incision, local injection with Poly(A) SPOT-ON (10 μg), but not scrambled SPOT-ON (10 μg), reduces mechanical hypersensitivity, contributed to resolution of pain sensitization, and blocked development of hyperalgesic priming when animals were challenged with PGE2 at day 15. *P<0.05, **P<0.01, significantly different from incision+scramble group analyzed by two-way ANOVA followed by Bonferroni post hoc test. (FIGS. 8K-L) Intraplantar injection of the Poly(A) SPOT-ON, but not scrambled SPOT-ON, significantly reduces the development of paw guarding following surgery as well as PGE2-induced priming. *P<0.05, **P<0.01, significantly different from incision+scramble group analyzed by two-way ANOVA followed by Bonferroni post hoc test. (FIGS. 8M-N) Intraplantar injection of the Poly(A) SPOT-ON, but not scrambled SPOT-ON, significantly reduces the presence of facial grimace following surgery and after priming with PGE2. *P<0.05, **P<0.01, significantly different from incision+scramble group analyzed by two-way ANOVA followed by Bonferroni post hoc test. (FIG. 8O) Paw incision significantly increases the temperature in the incised paw of mice 24 h after surgery. Under these conditions, local administration of the Poly(A) SPOT-ON, but not scrambled SPOTON, significantly decreased the incised paw temperature 24 h after surgery. (FIG. 8P) Quantification of incised and non-incised paw temperature from scrambled and SPOT-ON groups 24 h after surgery. *P<0.05, **P<0.01, significantly different from incision+scramble group analyzed by Student's t test. n=6 per group. For all graphs showing in the figure, data are plotted as mean±s.e.m.

(FIG. 9A) The Poly(A) SPOT-ON (10 μg) inhibits the mechanical hypersensitivity produced by intraplantar capsaicin (5 μg) and ((FIG. 9B) blocks the development of hyperalgesic priming. CGRP8-37 (1 μg) has a transient antinociceptive effect at 3 h post capsaicin with no changes after the precipitation of priming with PGE2. *P<0.05, **P<0.01, significantly different from scramble SPOT-ON+capsaicin (CAP) group analyzed by two-way ANOVA followed by Bonferroni post hoc test. (FIG. 9C) The Poly(A) SPOT-ON and CGRP8-37 attenuate the thermal hypersensitivity produced by capsaicin. *P<0.05, significantly different from Poly(A) SPOT-ON+capsaicin (CAP) group and &P<0.05, significantly different from baseline (BL) analyzed by two-way ANOVA followed by Bonferroni post hoc test. Not significantly different (NS) compared to baseline (BL). (FIG. 9D) No changes in thermal hypersensitivity are detected after priming revealed by PGE2. (FIG. 9E) The Poly(A) SPOT-ON and CGRP8-37 block the transient increase in paw temperature produced by intraplantar capsaicin administration. **P<0.01, significantly different from the non-injected paw or the Poly(A) SPOTON injected paw analyzed by one-way ANOVA followed by Bonferroni post hoc test. Not significantly different (NS) compared to non-injected paw. (FIG. 9F) No changes in paw temperature are present after priming (injected vs. non-injected paw). n=6 per group. For all graphs shown in the figure, data are plotted as mean±s.e.m.

DETAILED DESCRIPTION OF ILLUSTRATIVE EMBODIMENTS

Figure 1:
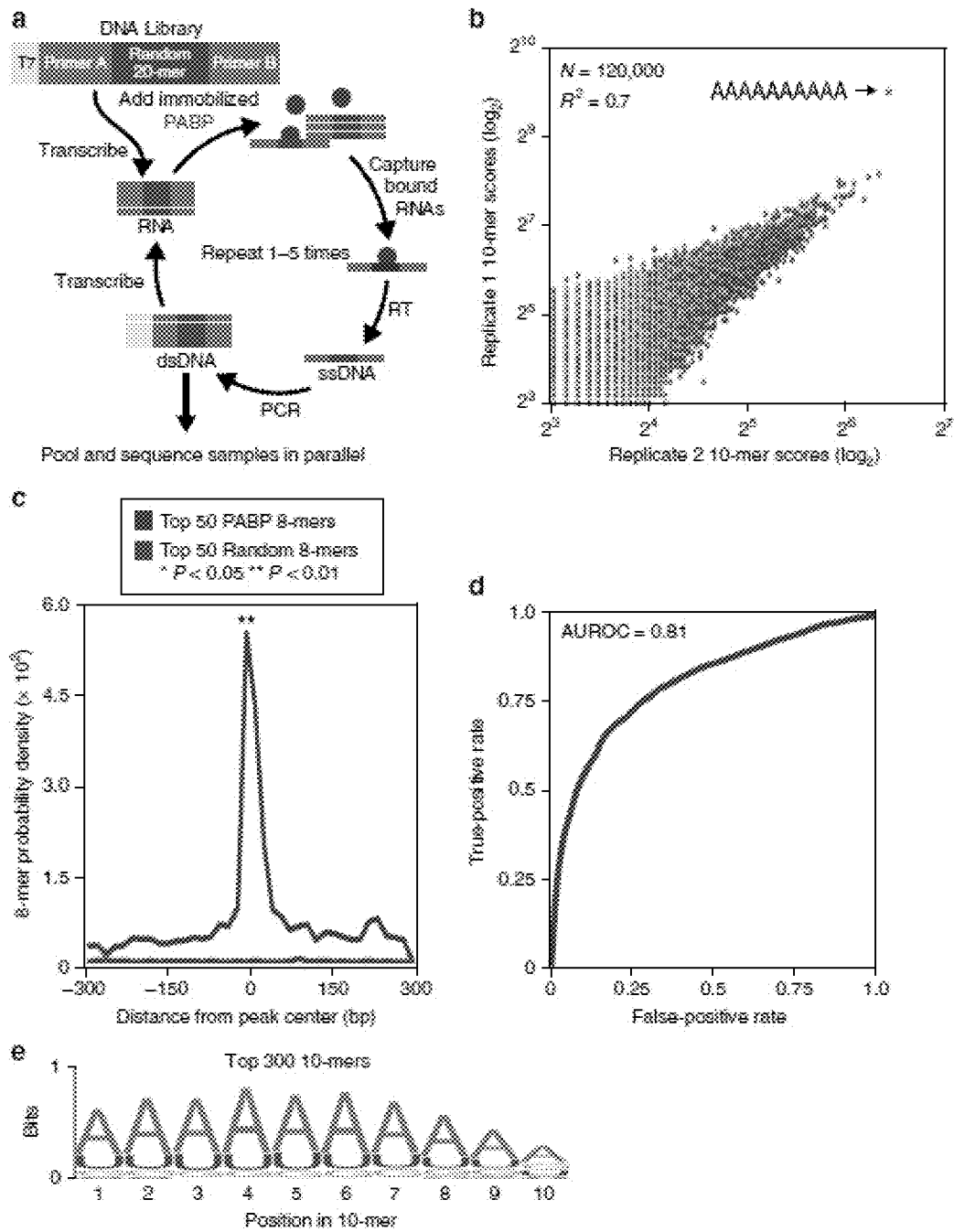
FIGS. 1A-E. Unbiased assessment of PABP specificity and in vivo confirmation.

As discussed above, little is known regarding the role of PABPs in induced CNS plasticity. The inventors hypothesized that the binding specificity of RNA-binding proteins in general can be used to guide the design of chemically-stabilized RNA. As a proof of concept, they examined the specificity of PABP using functional genomics to probe specificity in an unbiased way. Based on this information, they generated and characterized a chemically-stabilized RNA substrate that binds to PABP with high specificity in vitro and impairs nascent translation in a PABP-dependent mechanism in cells. PABP is expressed throughout the peripheral nervous system and the inventors target its function in mice in peripheral axons. They demonstrate that the effects of the RNA decoy on translation are specific to the initiation phase of translation and that axonal protein synthesis is impaired in nociceptor neurons. The Poly(A) SPOT-ON impairs pain sensitization in multiple models of tissue injury in vivo. Collectively, these experiments provide a guide for the rational design of RNA-binding protein inhibitors for use in cells or living animals.

I. RNA Binding Proteins

A. Poly-A Binding Protein

Poly(A)-binding protein (PAB or PABP) is an RNA-binding protein which binds to the poly(A) tail of mRNA. The poly(A) tail is located on the 3' end of mRNA and is 200-250 nucleotides long. The binding protein is also involved in mRNA precursors by helping polyadenylate polymerase add the poly(A) nucleotide tail to the pre-mRNA before translation. The nuclear isoform selectively binds to around 50 nucleotides and stimulates the activity of polyadenylate polymerase by increasing its affinity towards RNA. Poly(A)-binding protein is also present during stages of mRNA metabolism including nonsense-mediated decay and nucleocytoplasmic trafficking. The poly(A)-binding protein may also protect the tail from degradation and regulate mRNA production. Without these two proteins in-tandem, then the poly(A) tail would not be added and the RNA would degrade quickly.

The PABPN1 gene is located on the long (q) arm of chromosome 14 at position 11.2. More precisely, the PABPN1 gene is located from base pair 23,320,188 to base pair 23,326,185 on chromosome 14.

Cytosolic poly-A binding protein (PABPC) is made up of four RNA recognition motifs (RRMs) and a C-terminal region known as the PABC domain. RRM is the most common motifs for RNA recognition and is usually made up of 90-100 amino acids. Previous solution NMR and X-ray crystallography studies have shown that RRMs are globular domains, each composed of 4 anti-parallel β sheets that are backed by 2 α-helices. The central two β-strands, connected by a short linker, of each RRM forms a trough-like surface that's thought to be responsible for binding to the poly(A) oligonucleotides. The polyadenylate RNA adopts an extended conformation running the length of the molecular trough. Adenine recognition is primarily mediated by contacts with conserved residues found in the RNP motifs of the two RRMs. In vitro studies have shown the binding affinities to be on the order of 2-7 nM, while affinity for poly(U), poly(G), and poly(C) were reportedly lower or undetectable in comparison. This shows that the poly(A)-binding protein is specific to poly(A) oligonucleotides and not others. Since the two central β-strands are used for poly(A) oligonucleotide binding, the other face of the protein is free for protein-protein interactions.

The PABC domain is approximately 75 amino acids and consists of 4 or 5 α-helices depending on the organism—human PABCs have 5, while yeast has been observed to have 4. This domain does not contact RNA, and instead, it recognizes 15 residues sequences that are a part of the PABP interaction motif (PAM-2) found on such proteins as eukaryotic translation termination factor (eRF3) and PABP interacting proteins 1 and 2 (PAIP 1, PAIP2).

The structure of human poly(A)-binding protein found in the nucleus (PABPN1) has yet to be well determined but it has been shown to contain a single RRM domain and an arginine rich carboxy-terminal domain. They are thought to be structurally and functionally different from poly-A binding proteins found in the cytosol.

The expression of mammalian poly(A)-binding protein is regulated at the translational level by a feed-back mechanism: the mRNA encoding PABP contains in its 5' UTR an A-rich sequence which binds poly(A)-binding protein. This leads to autoregulatory repression of translation of PABP.

The cytosolic isoform of eukaryotic poly(A)-binding protein binds to the initiation factor eIF4G via its C-terminal domain. eIF4G is a component of the eIF4F complex, containing eIF4E, another initiation factor bound to the 5' cap on the 5' end of mRNA. This binding forms the characteristic loop structure of eukaryotic protein synthesis. Poly(A)-binding proteins in the cytosol compete for the eIF4G binding sites. This interaction enhances both the affinity of eIF4E for the cap structure and PABP1 for poly(A), effectively locking proteins onto both ends of the mRNA. As a result, this association may in part underlie the ability of PABP1 to promote small ribosomal (40S) subunit recruitment, which is aided by the interaction between eIF4G and eIF3. Poly(A)-binding protein has also been shown to interact with a termination factor (eRF3). The eRF3/PABP1 interaction may promote recycling of terminating ribosomes from the 3' to 5' end, facilitating multiple rounds of initiation on an mRNA. Alternatively, it may link translation to mRNA decay, as eRF3 appears to interfere with the ability of PABP1 to multimerise/form on poly(A), potentially leading to PABP1 dissociation, deadenylation and, ultimately, turnover.

OPMD. Oculopharyngeal muscular dystrophy (OPMD) is a genetic condition that occurs in adulthood often after the age of 40. This disorder usually leads to weaker facial muscles oftentimes showing as progressive eyelid drooping, swallowing difficulties, and proximal limb muscle weakness such as weak leg and hip muscles. People with this disorder are often hindered to the point that they have to use a cane in order to walk. OPMD has been reported in approximately 29 countries and the number affected varies widely by specific population. The disease can be inherited as an autosomal dominant or recessive trait.

Mutations. Mutations of poly(A)-binding protein nuclear 1 (PABPN1) can cause OPMD (oculopharyngeal muscular dystrophy). What makes the PABPN1 protein so different than all other genes with disease causing expanded polyalanine tracts, is that it is not a transcription factor. Instead, PABPN1 is involved in the polyadenylation of mRNA precursors.

Mutations in PABPN1 that cause this disorder, result when the protein has an extended polyalanine tract (12-17 alanines long vs. the expected amount of 10). The extra alanines cause PABPN1 to aggregate and form clumps within muscles because they are not able to be broken down. These clumps are believed to disrupt the normal function of muscle cells which eventually lead to cell death. This progressive loss of muscle cells most likely causes the weakness in muscles seen in patients with OPMD. It is still not known why this disorder only affects certain muscles like the upper leg and hip. In recent studies on OPMD in Drosophila, it has been shown that the degeneration of muscles within those who are affected may not solely be due to the expanded polyalanine tract. It may actually be due to the RNA-binding domain and its function in binding.

Current Studies. Recently, there has been considerable effort devoted to research of OPMD and how one might treat it. Myoblast Transplantation has been suggested and is in fact in clinical trials in France. This is done by taking myoblasts from a normal muscle cell and putting them into pharyngeal muscles and allowing them to develop to help form new muscle cells. There has also been testing of compounds, either existing or developed, to see if they might combat OPMD and its symptoms. Trehalose is a special form of sugar that has shown reduced aggregate formation and delayed pathology in the mouse model of OPMD. Doxycycline also played a similar role in delaying toxicity of OPMD in mouse models most likely due to stopping aggregate formation and reduced apoptosis. Many other compounds and methods are currently being researched and showing some success in clinical trials leading to optimism in curing this disease.

B. Eukaryotic Translation Initiation Factor 4E (eIF4E)

Eukaryotic translation initiation factor 4E, also known as eIF4E, is a protein that in humans is encoded by the EIF4E gene. Most eukaryotic cellular mRNAs are blocked at their 5'-ends with the 7-methyl-guanosine five-prime cap structure, m7GpppX (where X is any nucleotide). This structure is involved in several cellular processes including enhanced translational efficiency, splicing, mRNA stability, and RNA nuclear export. eIF4E is a eukaryotic translation initiation factor involved in directing ribosomes to the cap structure of mRNAs. It is a 24-kD polypeptide that exists as both a free form and as part of the eIF4F pre-initiation complex. Almost all cellular mRNA require eIF4E in order to be translated into protein. The eIF4E polypeptide is the rate-limiting component of the eukaryotic translation apparatus and is involved in the mRNA-ribosome binding step of eukaryotic protein synthesis. The other subunits of eIF4F are a 47-kD polypeptide, termed eIF4A, that possesses ATPase and RNA helicase activities, and a 220-kD scaffolding polypeptide, eIF4G.

Some viruses cut eIF4G in such a way that the eIF4E binding site is removed and the virus is able to translate its proteins without eIF4E. Also some cellular proteins, the most notable being heat shock proteins, do not require eIF4E in order to be translated. Both viruses and cellular proteins achieve this through an internal ribosome entry site in the RNA.

Since eIF4E is an initiation factor that is relatively low in abundance, eIF4E is a potential target for transcriptional control. Regulation of eIF4E may be achieved via three distinct mechanisms: transcription, phosphorylation, and inhibitory proteins.

The mechanisms responsible for eIF4E transcriptional regulation are not entirely understood. However, several reports suggest a correlation between myc levels and eIF4E mRNA levels during the cell cycle. The basis of this relationship was further established by the characterization of two myc-binding sites (CACGTG E box repeats) in the promoter region of the eIF4E gene. This sequence motif is shared with other in vivo targets for myc and mutations in the E box repeats of eIF4E inactivated the promoter region, thereby diminishing its expression.

Stimuli such as hormones, growth factors, and mitogens that promote cell proliferation also enhance translation rates by phosphorylating eIF4E. Although eIF4E phosphorylation and translation rates are not always correlated, consistent patterns of eIF4E phosphorylation are observed throughout the cell cycle; wherein low phosphorylation is seen during $G_0$ and M phase and wherein high phosphorylation is seen during $G_1$ and S phase. This evidence is further supported by the crystal structure of eIF4E which suggests that phosphorylation on serine residue 209 may increase the affinity of eIF4E for capped mRNA.

Assembly of the eIF4F complex is inhibited by proteins known as eIF4E-binding proteins (4E-BPs), which are small heat-stable proteins that block cap-dependent translation. Non-phosphorylated 4E-BPs interact strongly with eIF4E thereby preventing translation; whereas phosphorylated 4E-BPs bind weakly to eIF4E and thus do not interfere with the process of translation. Furthermore, binding of the 4E-BPs inhibits phosphorylation of Ser209 on eIF4E.

The role of eIF4E in cancer was established after Lazaris-Karatzas et al. made the discovery that overexpressing eIF4E causes tumorigenic transformation of fibroblasts. Since this initial observation, numerous groups have recapitulated these results in different cell lines. As a result, eIF4E activity is implicated in several cancers including cancers of the breast, lung, and prostate. In fact, transcriptional profiling of metastatic human tumors has revealed a distinct metabolic signature wherein eIF4E is known to be consistently up-regulated.

Fragile X mental retardation protein (FMR1) acts to regulate translation of specific mRNAs through its binding of eIF4E. FMRP acts by binding CYFIP1, which directly binds eIF4e at a domain that is structurally similar to those found in 4E-BPs including EIF4EBP3, EIF4EBP1, and EIF4EBP2. The FMRP/CYFIP1 complex binds in such a way as to prevent the eIF4E-eIF4G interaction, which is necessary for translation to occur. The FMRP/CYFIP1/eIF4E interaction is strengthened by the presence of mRNA(s). In particular, BC1 RNA allows for an optimal interaction between FMRP and CYFIP1. RNA-BC1 is a non-translatable, dendritic mRNA, which binds FMRP to allow for its association with a specific target mRNA. BC1 may function to regulate FMRP and mRNA interactions at synapse(s) through its recruitment of FMRP to the appropriate mRNA.

In addition, FMRP may recruit CYFIP1 to specific mRNAs in order to repress translation. The FMRP-CYFIP1 translational inhibitor is regulated by stimulation of neuron(s). Increased synaptic stimulation resulted in the dissociation of eIF4E and CYFIP1, allowing for the initiation of translation.

C. HuD or ELAV Like RNA Binding Protein 4 (Elav14)

HuD otherwise known as ELAV-like protein 4 is a protein that in humans is encoded by the ELAVL4 gene. The HuD/ELAVL4 protein is an RNA-binding protein. HuD contains three RRM protein domains, enabling RNA binding. HuD is expressed only in neurons and it binds to AU-rich element-containing mRNAs. As a result of this interaction the half-life of the transcript is increased. HuD is important in neurons during brain development and plasticity.

D. HuR or ELAV Like RNA Binding Protein 1 (Elav11)

ELAV-like protein 1 or HuR (human antigen R) is a protein that in humans is encoded by the ELAVL1 gene. The protein encoded by this gene is a member of the ELAVL protein family. This encoded protein contains 3 RNA-binding domains and binds cis-acting AU-rich elements. One of its best-known functions is to stabilize mRNAs including several cytokines, in order to regulate gene expression and is involved in the maintenance of inflammation and in proper functioning of the immune system.

E. Cytoplasmic Polyadenylation Element Binding Protein (CPEB)

CPEB, or cytoplasmic polyadenylation element binding protein, is a highly conserved RNA-binding protein that promotes the elongation of the polyadenine tail of messenger RNA. CPEB most commonly activates the target RNA for translation, but can also act as a repressor, dependent on its phosphorylation state. In animals, CPEB is expressed in several alternative splicing isoforms that are specific to particular tissues and functions, including the self-cleaving Mammalian CPEB3 ribozyme. CPEB was first identified in *Xenopus* oocytes and associated with meiosis; a role has also been identified in the spermatogenesis of *Caenorhabditis elegans*.

CPEB is involved in closed-loop regulation of mRNAs that keeps them inactive. The closed-loop structure between the 3'UTR and 5'UTR inhibits translation. This has been observed in *Xenopus laevis* in which eIF4E bound to the 5' cap interacts with Maskin bound to CPEB on the 3' UTR creating translationally inactive transcripts. This translational inhibition is lifted once CPEB is phosphorylated, displacing the Maskin binding site, allowing for the polymerization of the polyA tail, which can recruit the translational machinery by means of PABP. However, it is important to note that this mechanism has been under great scrutiny.

*Drosophila* Orb2 binds to genes implicated in long-term memory. An isoform of CPEB found in the neurons of the sea slug *Aplysia californica*, as well as in *Drosophila*, mice, and humans, contains an N-terminal domain not found in other isoforms that shows high sequence similarity to prion proteins. Experiments with the *Aplysia* isoform expressed in yeast reveal that CPEB has a key property associated with prions: it can cause other proteins to assume alternate protein conformations that are heritable in successive generations of yeast cells. Furthermore, the functional RNA-binding form of the CPEB protein may be the prion-like state. These observations have led to the suggestion that long-lasting bistable prionlike proteins play a role in the formation of long-term memory. It has been suggested that both memory storage and its underlying synaptic plasticity are mediated by the increase in CPEB.

CPEB has been shown to interact with PUM2, PARN, GLD-2, symplekin and eIF4E binding protein F. Fragile X Mental Retardation Protein (FMRP)

FMR1 (fragile X mental retardation 1) is a human gene that codes for a protein called fragile X mental retardation protein, or FMRP. This protein, most commonly found in the brain, is essential for normal cognitive development and female reproductive function. Mutations of this gene can lead to fragile X syndrome, intellectual disability, premature ovarian failure, autism, Parkinson's disease, developmental delays and other cognitive deficits. The FMR1 premutation is associated with a wide spectrum of clinical phenotypes that affect more than two million people worldwide.

FMRP has a diverse array of functions throughout different areas of the neuron; however, these functions have not been fully characterized. FMRP has been suggested to play roles in nucleocytoplasmic shuttling of mRNA, dendritic mRNA localization, and synaptic protein synthesis. Studies of Fragile X syndrome have significantly aided in the understanding of the functionality of FMRP through the observed effects of FMRP loss on neurons. A mouse model of fragile X mental retardation implicated the involvement of FMRP in synaptic plasticity. Synaptic plasticity requires the production of new proteins in response to activation of synaptic receptors. It is the production of proteins in response to stimulation which is hypothesized to allow for the permanent physical changes and altered synaptic connections that are linked with the processes of learning and memory.

Group 1 metabotropic glutamate receptor (mGluR) signaling has been implicated in playing an important role in FMRP-dependent synaptic plasticity. Post-synaptic mGluR stimulation results in the up-regulation of protein synthesis through a second messenger system. A role for mGluR in synaptic plasticity is further evidenced by the observation of dendritic spine elongation following mGluR stimulation. Furthermore, mGluR activation results in the synthesis of FMRP near synapses. The produced FMRP associates with polyribosomal complexes after mGluR stimulation, proposing the involvement of fragile X mental retardation protein in the process of translation. This further advocates a role for FMRP in synaptic protein synthesis and the growth of synaptic connections. The loss of FMRP results in an abnormal dendritic spine phenotype. Specifically, deletion of the FMR1 gene in a sample of mice resulted in an increase in spine synapse number.

The proposed mechanism of FMRP's effect upon synaptic plasticity are through its role as a negative regulator of translation. FMRP is an RNA-binding protein which associates with polyribosomes. The RNA-binding abilities of FMRP are dependent upon its KH domains and RGG boxes. The KH domain is a conserved motif which characterizes many RNA-binding proteins. Mutagenesis of this domain resulted in impaired FMRP binding to RNA.

FMRP has been shown to inhibit translation of mRNA. Mutation of the FMRP protein resulted in the inability to repress translation as opposed to the wild-type counterpart which was able to do so. As previously mentioned, mGluR stimulation is associated with increased FMRP protein levels. In addition, mGluR stimulation results in increased levels of FMRP target mRNAs. A study found basal levels of proteins encoded by these target mRNAs to be significantly elevated and improperly regulated in FMRP deficient mice.

FMRP translation repression acts by inhibiting the initiation of translation. FMRP directly binds CYFIP1, which in turn binds the translation initiation factor eIF4E. The FMRP-CYFIP1 complex prohibits eIF4E-dependent initiation, thereby acting to repress translation. When applied to the observed phenotype in fragile X Syndrome, the excess protein levels and reduction of translational control can be explained by the loss of translational repression by FMRP in fragile X syndrome. FMRP acts to control translation of a large group of target mRNAs; however the extent of FMRPs translational control is unknown. The protein has been shown to repress the translation of target mRNAs at synapses, including those encoding the cytoskeletal proteins Arc/Arg3.1 and MAP1B, and the CaM kinase II. In addition, FMRP binds PSD-95 and GluR1/2 mRNAs. Importantly, these FMRP-binding mRNAs play significant roles in neuronal plasticity.

FMRP translational control has been shown to be regulated by mGluR signaling. mGluR stimulation may result in the transportation of mRNA complexes to synapses for local protein synthesis. FMRP granules have been shown to localize with MAP1B mRNA and ribosomal RNA in dendrites, suggesting this complex as a whole may need to be transported to dendrites for local protein synthesis. In addition, microtubules were found to be a necessary component for the mGluR-dependent translocation of FMRP into dendrites. FMRP may play an additional role in local protein synthesis by aiding in the association of mRNA cargo and microtubules. Thus, FMRP is able to regulate transport efficacy, as well as repression of translation during transport. Finally, FMRP synthesis, ubiquitination, and proteolysis occur rapidly in response to mGluR signaling, suggesting an extremely dynamic role of the translational regulator.

The FMR1 gene is located on the X chromosome and contains a repeated CGG trinucleotide. In most people, the CGG segment is repeated approximately 5-44 times. Higher numbers of repeats of the CGG segment are associated with impaired cognitive and reproductive function. If a person has 45-54 repeats this is considered the "gray zone" or borderline risk, 55-200 repeats is called premutation, and more than 200 repeats is considered a full mutation of the FMR1 gene according to the American College of Medical Genetics and Genomics. The first complete DNA sequence of the repeat expansion in someone with the full mutation was generated by scientists in 2012 using SMRT sequencing. This is an example of a Trinucleotide repeat disorder. Trinucleotide repeat expansion is likely a consequence of strand slippage either during DNA repair or DNA replication.

FMR1 is a chromatin-binding protein that functions in the DNA damage response. FMR1 occupies sites on meiotic chromosomes and regulates the dynamics of the DNA damage response machinery during spermatogenesis. The FMR1 gene can be found on the long (q) arm of the X chromosome at position 27.3, from base pair 146,699,054 to base pair 146,738,156

Almost all cases of fragile X syndrome are caused by expansion of the CGG trinucleotide repeat in the FMR1 gene. In these cases, CGG is abnormally repeated from 200 to more than 1,000 times. As a result, this part of the FMR1 gene is methylated, which silences the gene (it is turned off and does not make any protein). Without adequate FMR1, severe learning disabilities or intellectual disabilities can develop, along with physical abnormalities seen in fragile X syndrome.

Fewer than 1% of all cases of fragile X syndrome are caused by mutations that delete part or all of the FMR1 gene, or change a base pair, leading to a change in one of the amino acids in the gene. These mutations disrupt the 3-dimensional shape of FMRP or prevent the protein from being synthesized, leading to the signs and symptoms of fragile X syndrome.

A CGG sequence in the FMR1 gene that is repeated between 55 and 200 times is described as a premutation. Although most individuals with the premutation are intellectually normal, some of these individuals have mild versions of the physical features seen in fragile X syndrome (such as prominent ears) and may experience mental health problems such as anxiety or depression.

Premutations are associated with an increased risk of fragile X-associated tremor/ataxia syndrome (FXTAS).

FXTAS is characterized by ataxia (loss of coordination), tremor, memory loss, loss of sensation in the lower extremities (peripheral neuropathy) and mental and behavioral changes. The disorder usually develops late in life. Premature ovarian aging [edit]

The FMR1 gene plays a very important role in ovarian function, independent from cognitive/neurological effects. Minor expansions of CGG repeats that do not cause fragile X syndrome are associated with an increased risk for premature ovarian aging, also called occult primary ovarian insufficiency, a condition in which women prematurely deplete their ovarian function.

A very specific sub-genotype of FMR1 has been found to be associated with polycystic ovarian syndrome (PCOS). The gene expression, called heterozygous-normal/low may cause PCOS-like excessive follicle-activity and hyperactive ovarian function when women are younger.

II. Pain

Pain is an unpleasant feeling often caused by intense or damaging stimuli. The International Association for the Study of Pain's widely used definition states: "Pain is an unpleasant sensory and emotional experience associated with actual or potential tissue damage or described in terms of such damage."

Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation in the United States. It is a major symptom in many medical conditions and can significantly interfere with a person's quality of life and general functioning. Psychological factors such as social support, hypnotic suggestion, excitement, or distraction can significantly modulate pain's intensity or unpleasantness.

The International Association for the Study of Pain (IASP) has classified pain according to specific characteristics: (a) region of the body involved (e.g., abdomen, lower limbs), (b) system whose dysfunction may be causing the pain (e.g., nervous, gastrointestinal), (c) duration and pattern of occurrence, (d) intensity and time since onset, and (e) etiology. This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system (neuropathic pain, see hereunder) or by its abnormal function (dysfunctional pain, like in fibromyalgia, irritable bowel syndrome, tension type headache, etc.).

A. Chronic Pain

Pain is usually transitory, lasting only until the noxious stimulus is removed or the underlying damage or pathology has healed, but some painful conditions, such as rheumatoid arthritis, peripheral neuropathy, cancer and idiopathic pain, may persist for years. Pain that lasts a long time is called chronic, and pain that resolves quickly is called acute. Traditionally, the distinction between acute and chronic pain has relied upon an arbitrary interval of time from onset; the two most commonly used markers being 3 months and 6 months since the onset of pain, though some theorists and researchers have placed the transition from acute to chronic pain at 12 months. Others apply acute to pain that lasts less than 30 days, chronic to pain of more than six months duration, and subacute to pain that lasts from one to six months. A popular alternative definition of chronic pain, involving no arbitrarily fixed durations is "pain that extends beyond the expected period of healing."

Chronic pain may be classified as cancer pain or benign.

B. Nociceptive Pain Nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). As subset of nocicipetive pain is called "inflammatory" pain, as it results from tissue damage and the response of innate inflammatory responses. Nociceptive pain may also be divided into "visceral," "deep somatic" and "superficial somatic" pain. Visceral structures are highly sensitive to stretch, ischemia and inflammation, but relatively insensitive to other stimuli that normally evoke pain in other structures, such as burning and cutting. Visceral pain is diffuse, difficult to locate and often referred to a distant, usually superficial, structure. It may be accompanied by nausea and vomiting and may be described as sickening, deep, squeezing, and dull. Deep somatic pain is initiated by stimulation of nociceptors in ligaments, tendons, bones, blood vessels, fasciae and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns.

C. Neuropathic Pain

Neuropathic pain is pain caused by damage or disease that affects the somatosensory system. It may be associated with abnormal sensations called dysesthesia, and pain produced by normally non-painful stimuli (allodynia). Neuropathic pain may have continuous and/or episodic (paroxysmal) components. The latter are likened to an electric shock. Common qualities include burning or coldness, "pins and needles" sensations, numbness and itching. Nociceptive pain, by contrast, is more commonly described as aching.

Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain. Central neuropathic pain is found in spinal cord injury, multiple sclerosis, and some strokes. Aside from diabetes (see diabetic neuropathy) and other metabolic conditions, the common causes of painful peripheral neuropathies are herpes zoster infection, HIV-related neuropathies, nutritional deficiencies, toxins, remote manifestations of malignancies, immune mediated disorders and physical trauma to a nerve trunk.

Neuropathic pain is common in cancer as a direct result of cancer on peripheral nerves (e.g., compression by a tumor), or as a side effect of chemotherapy, radiation injury or surgery. After a peripheral nerve lesion, aberrant regeneration may occur. Neurons become unusually sensitive and develop spontaneous pathological activity, abnormal excitability, and heightened sensitivity to chemical, thermal and mechanical stimuli. This phenomenon is called "peripheral sensitization."

The (spinal cord) dorsal horn neurons give rise to the spinothalamic tract (STT), which constitutes the major ascending nociceptive pathway. As a consequence of ongoing spontaneous activity arising in the periphery, STT neurons develop increased background activity, enlarged receptive fields and increased responses to afferent impulses, including normally innocuous tactile stimuli. This phenomenon is called central sensitization. Central sensitization is an important mechanism of persistent neuropathic pain.

Other mechanisms, however, may take place at the central level after peripheral nerve damage. The loss of afferent signals induces functional changes in dorsal horn neurons. A decrease in the large fiber input decreases activity of interneurons inhibiting nociceptive neurons, i.e., loss of afferent inhibition. Hypoactivity of the descending antinociceptive systems or loss of descending inhibition may be another factor. With loss of neuronal input (deafferentation) the STT neurons begin to fire spontaneously, a phenomenon designated "deafferentation hypersensitivity." Neuroglia ("glial cells") may play a role in central sensitization. Peripheral nerve injury induces glia to release proinflammatory cytokines and glutamate—which, in turn influence neurons.

D. Current Therapies

The following is a discussion of different therapies currently applied against nociceptive pain conditions. Such is exemplary and not limiting. Currently, there are a wide number of agents effective at treating nociceptive pain. These include salicylates, such as Aspirin (acetylsalicylic acid), Diflunisal and Salsalate, Propionic acid derivatives (Ibuprofen, Dexibuprofen, Naproxen, Fenoprofen, Ketoprofen, Dexketoprofen, Flurbiprofen, Oxaprozin, Loxoprofen), Acetic acid derivatives, (Indomethacin, Tolmetin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives or "Fenamates" (Mefenamic acid, Meclofenamic acid, Flufenamic acid, Tolfenamic acid), Selective COX-2 inhibitors (Celecoxib, Rofecoxib, Valdecoxib, Parecoxib, Lumiracoxib, Etoricoxib, Firocoxib), Sulphonanilides such as Nimesulide, and a range of other compounds (Licofelone, Lysine clonixinate, Hyperforin, Figwort).

Opioids, also known as narcotics, are increasingly recognized as important treatment options for chronic pain. Opioids, along with anticonvulsants and antidepressants are the most consistently effective class of drugs for neuropathic pain. Opioids must be used only in appropriate individuals and under close medical supervision. Several opioids, particularly methadone, and ketobemidone possess NMDA antagonism in addition to their μ-opioid agonist properties. Methadone does so because it is a racemic mixture; only the l-isomer is a potent μ-opioid agonist. The d-isomer does not have opioid agonist action and acts as an NMDA antagonist; d-methadone is analgesic in experimental models of chronic pain. Clinical studies are in progress to test the efficacy of d-methadone in neuropathic pain syndromes.

III. Inhibitory Oligonucleotides

A. SPOT-ONs

SPOT-ONs (specificity derived competitive inhibitor oligonucleotides) will be employed to target PAB in accordance with the present disclosure. To overcome the intrinsic short half-life of RNA, the inventors modify RNA oligonucleotides in several ways. First, to inhibit exonucleases that operate in the 5'→3' direction (e.g., Xrn1) and 3'→5' (e.g., Ccr4; Pan2/3), the backbone on the terminal bases is modified into a phosphorothioate wherein of the non-bridging oxygens is replaced by a sulfur. The sulfurization of the internucleotide bond dramatically reduces the action of exonucleases (Dagle et al., 1991). To further increase stability, all of the 2' hydroxyl groups are replaced with 2'O-Methyl modifications. This modification is ubiquitous in therapeutic oligonucleotides as it eliminates the potential for spontaneous or enzyme catalyzed general base hydrolysis. Collectively, these modifications endow single-stranded RNA with extraordinary stability.

Highly modified RNAs similar to SPOT-ONs are used for several applications. These include modified miRNA/siRNAs, antisense oligonucleotides (ASOs), and nucleic acid aptamers. In the case of miRNAs/siRNAs/ASOs the oligonucleotides target mRNA encoding a given gene. Thus, the mechanism of action is completely and fundamentally different. Thus, the problems that plague these technologies regarding uptake, delivery, and specificity likely do not apply to SPOT-ONs which are much smaller and do not require extensive base pair interactions to achieve their biological functions. An alternative strategy to impair PABP is the delivery of ASOs that reduce PABP expression. However, in almost all cell types PABP is expressed via multiple paralogs necessitating complex strategies to simultaneously knock-down multiple gene products.

Nucleic acid aptamers are similar to SPOT-ONs as they target proteins that may or may not normally associate with RNA. While SPOT-ONs are based on disrupting known biological mechanisms, aptamers are derived from a random in vitro selection process that assumes nothing about the biological functions of a given target. As a result, aptamers tend to be much larger (usually 40-100 bases) and have shown some promise in the clinic. Pegaptanib, a therapeutic aptamer against Vascular Endothelial Growth Factor (VEGF), become the first FDA approved RNA aptamer for use against age-related macular degeneration (AMD). There are multiple RNA aptamers under clinical and preclinical trials for the treatment of diseases including diabetes and cancer. SPOT-ONs have numerous advantages to RNA aptamers as they do not rely on complex secondary and tertiary structures to achieve specificity.

A minimum of 11-12 adenosines are required for high affinity binding to PABP32. The Poly(A) SPOT-ON mimics the composition of the Poly(A) tail. The inventors competitor inhibitor SPOT-ON against PABP is encoded by the following synthetic modified RNA:

[mA]*[mA][mA][mA][mA][mA][mA][mA][mA][mA]
[mA]*[mA] (SEQ ID NO: 1)

Figure 10:
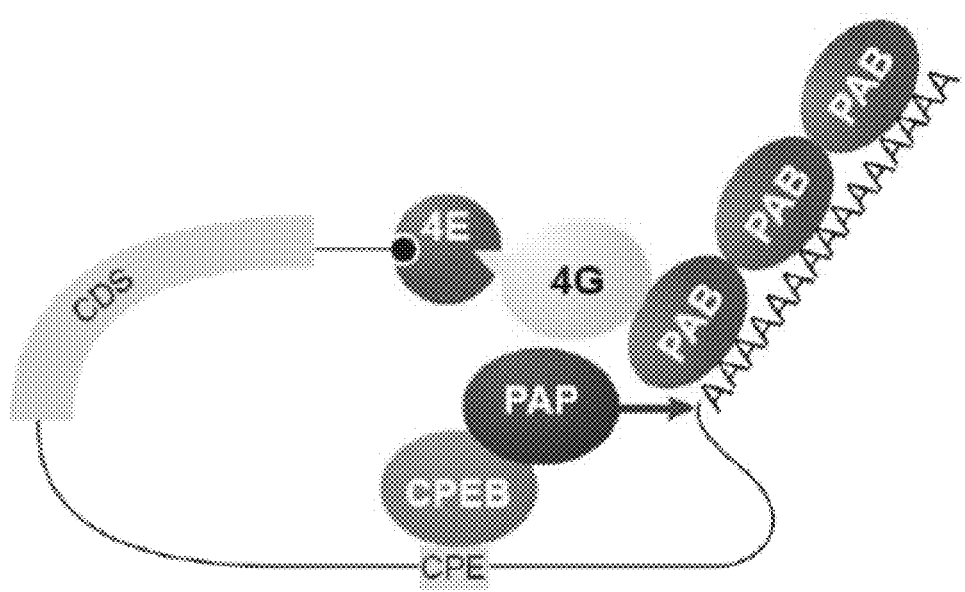
FIG. 10. The role of the Poly(A) tail. In the cytoplasm, PAB directly associates with 3' poly adenosine track to promote cap-dependent translation along with eIF4E/G (light blue and yellow respectively). The amount of PAB (red) bound to a given transcript (black line) is proportional to the length of the poly(A) tail. This length is subject to change over time and can be regulated by RNA binding proteins such as CPEB (green) which recruit regulatory polymerases (PAP—dark blue). In many cell types, including neurons, regulatory polymerases participate in signal transduction cascades to trigger the extension of the poly(A) tail in response to extracellular cues. This is known to enhance association of the transcript with PABP and stimulate protein synthesis. Thus, PABP resides at the heart of a regulatory control network responsible for regulated protein synthesis. (Poly(A) tail illustrated=SEQ ID NO: 2)

Each base is bracketed, a star denotes a phosphorothioate bond, and m denotes 2'O-Methyl modifications. As shown in FIG. 10, PAB directly associates with 3' poly-adenosine track in the cytoplasm to promote cap-dependent translation along with eIF4E/G. The amount of PAB bound to a given transcript is proportional to the length of the poly(A) tail. This length is subject to change over time and can be regulated by RNA binding proteins such as CPEB, which recruit regulatory polymerases (PAP). In many cell types, including neurons, regulatory polymerases participate in signal transduction cascades to trigger the extension of the poly(A) tail in response to extracellular cues. This is known to enhance association of the transcript with PABP and stimulate protein synthesis. Thus, PABP resides at the heart of a regulatory control network responsible for regulated protein synthesis.

Nociceptors, the neurons that are responsible for sensing pain and sending the "pain signal" on to the central nervous system, are key neurons for the development and maintenance of pathological pain. These neurons readily change their sensitivity and firing properties after injury and this change can persist for even long after an injury resolves. This type of plasticity requires changes in gene expression in these neurons and over the course of the past decade the inventor has shown that translation regulation pathways play a key role in this pathological pain plasticity. The SPOT-ON approach allows for long lasting modulation of specific translation regulation signaling through the disruption of RBP-RNA interactions.

B. Targeting Ligands

In one embodiment, the SPOT-ON may be linked to a moiety that will target the SPOT-ON to a cell of interest, such as by 5' and 3' conjugation. Such targeting strategies have been employed successfully to direct cancer therapies to the target cells. Examples of ligands used include biotin, folic acid, carbohydrates (Lex and ManLAM), RR-11a, anisamide, myristic acid, capsaicin and dimannose.

Given the potential sensitivity of small oligonucleotides to modifications, chemistries have been designed to permit attachment of targeting agents. Some examples include hydrazide-aldehyde, amino-carboxyl, thiol-maleimide, thiol-thiol, gold-thiol and click chemistries.

IV. Methods of Treating Subjects

A. Method of Administration

Administration of these compositions according to the present invention will be via any common route so long as the target tissue is available via that route. Such routes include oral, nasal, buccal, rectal, vaginal or topical route. Alternatively, administration may be by orthotopic, transdermal, intradermal, subcutaneous, intramuscular, intraperitoneal, intrathecal or intravenous injection. Such compositions would normally be administered as pharmaceutically acceptable compositions, described supra. Of particular interest is transdermal, intraperitoneal, intravenous or oral administration.

With regard to transdermal delivery, a patch is particularly contemplated. There are five main types of transdermal patches. In the Single-layer Drug-in-Adhesive, the adhesive layer of this system also contains the drug. In this type of patch, the adhesive layer not only serves to adhere the various layers together, along with the entire system to the skin, but is also responsible for the releasing of the drug. The adhesive layer is surrounded by a temporary liner and a backing. In Multi-layer Drug-in-Adhesive, the multi-layer drug-in adhesive patch is similar to the single-layer system in that both adhesive layers are also responsible for the releasing of the drug. One of the layers is for immediate release of the drug and other layer is for control release of drug from the reservoir. The multi-layer system is different however that it adds another layer of drug-in-adhesive, usually separated by a membrane (but not in all cases). This patch also has a temporary liner-layer and a permanent backing.

Unlike the Single-layer and Multi-layer Drug-in-adhesive systems, the reservoir transdermal system has a separate drug layer. The drug layer is a liquid compartment containing a drug solution or suspension separated by the adhesive layer. This patch is also backed by the backing layer. In this type of system, the rate of release is zero order.

The Matrix system has a drug layer of a semisolid matrix containing a drug solution or suspension. The adhesive layer in this patch surrounds the drug layer partially overlaying it. Also known as a monolithic device.

In Vapor Patches, the adhesive layer not only serves to adhere the various layers together but also to release vapour. The vapour patches are new on the market and they release essential oils for up to 6 hours. The vapour patches release essential oils and are used in cases of decongestion mainly. Other vapour patches on the market are controller vapour patches that improve the quality of sleep. Vapour patches that reduce the quantity of cigarettes that one smokes in a month are also available on the market.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

B. Formulations

Where clinical applications are contemplated, formulations will be prepared in a form appropriate for the intended application. Generally, this will entail preparing compositions that are essentially free of pyrogens, as well as other impurities that could be harmful to cells, humans or animals.

One will generally desire to employ appropriate salts and buffers to render SPOT-ONs stable and allow for uptake by target cells. Aqueous compositions of the present disclosure comprise an effective amount of the SPOT-ONs, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the enzymes or cells.

The active compositions of the present disclosure may include classic pharmaceutical preparations. By way of illustration, solutions of the active compounds as free base or pharmacologically acceptable salts can be prepared in water suitably mixed with a surfactant, such as hydroxypropylcellulose. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agent, for example, a paraben, chlorobutanol, phenol, sorbic acid, thimerosal, and the like. It may be desired to include isotonic agents, for example, sugars or sodium chloride.

Sterile solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably used in a manner compatible with the dosage formulation and in such amount as is therapeutically effective (see for example, "Remington's Pharmaceutical Sciences" 15th Edition, pages 1035-1038 and 1570-1580). Some variation in dosage may occur depending on the particular target cell. The person responsible for administration will, in any event, determine the appropriate dose for the individual subject. Moreover, for human administration, preparations should meet sterility, pyrogenicity, general safety and purity standards as required by FDA Office of Biologics standards.

C. Combination Therapies

Treating pain and avoiding tolerance to pain killers are major issues in clinical medicine. One goal of current research is to find ways to improve the efficacy of pain relief, as well as prevent the development of tolerance or addiction, and reduce side effects. One way is by combining such traditional therapies with the SPOT-ONs of the present disclosure. In this context, it is contemplated that SPOT-ON may be used in a combination therapy with another pain agent, such as an opiate, an NSAID or a steroid.

The therapies would be provided in a combined amount effective to reduce pain, prevent tolerance and to reduce side effects associated with the other agents, including but not limited to addiction and withdrawal. This process may involve contacting the patient with the agents/therapies at the same time. This may be achieved by contacting the patient with a single composition or pharmacological formulation that includes both agents, or by contacting the cell with two distinct compositions or formulations, at the same time, wherein one composition includes the SPOT-ON and the other includes the other agent.

Alternatively, the SPOT-ON treatment may precede or follow the other treatment by intervals ranging from minutes to weeks. In embodiments where the agents are applied separately to the subject, one would generally ensure that a significant period of time did not expire between each delivery, such that the therapies would still be able to exert an advantageously combined effect on the subject. In such instances, it is contemplated that one would administer both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the SPOT-ON or the other therapy will be desired. Various combinations may be employed, where the SPOT-ON is "A," and the opioid therapy is "B," as exemplified below:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations, including chronic and continuous dosing of one or both agents, are contemplated. The following is a discussion of different therapies currently applied against different types of pain conditions. Such is exemplary and not limiting.

1. Inflammatory Pain

Currently, there are a wide number of agents effective at treating nociceptive/inflammatory pain. These include salicylates, such as Aspirin (acetylsalicylic acid), Diflunisal and Salsalate, Propionic acid derivatives (Ibuprofen, Dexibuprofen, Naproxen, Fenoprofen, Ketoprofen, Dexketoprofen, Flurbiprofen, Oxaprozin, Loxoprofen), Acetic acid derivatives, (Indomethacin, Tolmetin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives or "Fenamates" (Mefenamic acid, Meclofenamic acid, Flufenamic acid, Tolfenamic acid), Selective COX-2 inhibitors (Celecoxib, Rofecoxib, Valdecoxib, Parecoxib, Lumiracoxib, Etoricoxib, Firocoxib), Sulphonanilides such as Nimesulide, and a range of other compounds (Licofelone, Lysine clonixinate, Hyperforin, Figwort).

2. Neuropathic Pain

Neuropathic pain can be very difficult to treat with only 40-60% of patients achieving partial relief and determining the best treatment for individual patients remains challenging. Attempts to translate scientific studies into best practices are limited by factors such as differences in reference populations and a lack of head-to-head studies. Furthermore, multi-drug combinations and the needs of special populations, such as children, require more study.

It is common practice in medicine to designate classes of medication according to their most common or familiar use, e.g., as "antidepressants" and "anti-epileptic drugs" (AED's). These drugs have alternate uses to treat pain because the human nervous system employs common mechanisms for different functions, for example ion channels for impulse generation and neurotransmitters for cell-to-cell signaling. Favored treatments are certain antidepressants, e.g., tricyclics and selective serotonin-norepinephrine reuptake inhibitors (SNRI's), anticonvulsants, especially pregabalin (Lyrica) and gabapentin (Neurontin), and topical lidocaine. Opioid analgesics and tramadol are recognized as useful agents but are not recommended as first line treatments. Many of the pharmacologic treatments for chronic neuropathic pain decrease the sensitivity of nociceptive receptors, or desensitize C fibers such that they transmit fewer signals. Some drugs may exert their influence through descending pain modulating pathways. These descending pain modulating pathways originate in the brainstem.

Antidepressants. The functioning of antidepressants is different in neuropathic pain from that observed in depression. Activation of descending norepinephrinergic and serotonergic pathways to the spinal cord limit pain signals ascending to the brain. Antidepressants will relieve neuropathic pain in non-depressed persons.

In animal models of neuropathic pain it has been found that compounds which only block serotonin reuptake do not improve neuropathic pain. Similarly, compounds that only block norepinephrine reuptake also do not improve neuropathic pain. Dual serotonin-norepinephrine reuptake inhibitors such as duloxetine, venlafaxine, and milnacipran, as well as tricyclic antidepressants such as amitriptyline, nortriptyline, and desipramine improve neuropathic pain and are considered first-line medications for this condition. Bupropion has been found to have efficacy in the treatment of neuropathic pain. Tricyclic antidepressants may also have effects on sodium channels.

Anticonvulsants. Pregabalin (Lyrica) and gabapentin (Neurontin) work by blocking specific calcium channels on neurons and are preferred first-line medications for diabetic neuropathy. The anticonvulsants carbamazepine (Tegretol) and oxcarbazepine (Trileptal) are especially effective in trigeminal neuralgia. The actions of these two drugs are mediated principally through sodium channels.

Lamotrigine may have a special role in treating two conditions for which there are few alternatives, namely post stroke pain and HIV/AIDS-related neuropathy in patients already receiving antiretroviral therapy.

Opioids. Opioids, also known as narcotics, are increasingly recognized as important treatment options for chronic pain. They are not considered first line treatments in neuropathic pain but remain the most consistently effective class of drugs for this condition. Opioids must be used only in appropriate individuals and under close medical supervision. Several opioids, particularly methadone, and ketobemidone possess NMDA antagonism in addition to their µ-opioid agonist properties. Methadone does so because it is a racemic mixture; only the 1-isomer is a potent µ-opioid agonist. The d-isomer does not have opioid agonist action and acts as an NMDA antagonist; d-methadone is analgesic in experimental models of chronic pain. Clinical studies are in progress to test the efficacy of d-methadone in neuropathic pain syndromes.

Topical agents. In some forms of neuropathy, especially post-herpetic neuralgia, the topical application of local anesthetics such as lidocaine can provide relief. A transdermal patch containing lidocaine is available commercially in some countries. Repeated topical applications of capsaicin, are followed by a prolonged period of reduced skin sensibility referred to as desensitization, or nociceptor inactivation. Capsaicin not only depletes substance P but also results in a reversible degeneration of epidermal nerve fibers. Nevertheless, benefits appear to be modest with standard (low) strength preparations.

Cannabinoids. Marijuana's active ingredients are called cannabinoids. Unfortunately, strongly held beliefs make discussion of the appropriate use of these substances, in a medical context, difficult. Similar considerations apply to opioids. A recent study showed smoked marijuana is beneficial in treating symptoms of HIV-associated peripheral neuropathy. Nabilone is an artificial cannabinoid which is significantly more potent than delta-9-tetrahydrocannabinol (THC). Nabilone produces less relief of chronic neuropathic pain and had slightly more side effects than dihydrocodeine. The predominant adverse effects are CNS depression and cardiovascular effects which are mild and well tolerated but, psychoactive side effects limit their use. A complicating issue may be a narrow therapeutic window; lower doses decrease pain, but higher doses have the opposite effect.

Sativex, a fixed dose combination of delta-9-tetrahydrocannabinol (THC) and cannabidiol, is sold as an oromucosal spray. The product is approved in both Sweden and Canada as adjunctive treatment for the symptomatic relief of neuropathic pain in multiple sclerosis, and for cancer related pain. Long-term studies are needed to assess the probability of weight gain, unwanted psychological influences and other adverse effects.

Botulinum toxin type A. Botulinum toxin type A (BTX-A) is best known by its trade name, Botox. Local intradermal injection of BTX-A is helpful in chronic focal painful neuropathies. The analgesic effects are not dependent on changes in muscle tone. Benefits persist for at least 14 weeks from the time of administration. The utility of BTX-A in other painful conditions remains to be established.

NMDA antagonism. The N-methyl-D-aspartate (NMDA) receptor seems to play a major role in neuropathic pain and in the development of opioid tolerance. Dextromethorphan is an NMDA antagonist at high doses. Experiments in both animals and humans have established that NMDA antagonists such as ketamine and dextromethorphan can alleviate neuropathic pain and reverse opioid tolerance. Unfortunately, only a few NMDA antagonists are clinically available and their use is limited by a very short half life (dextromethorphan), weak activity (memantine) or unacceptable side effects (ketamine).

Reducing sympathetic nervous stimulation. In some neuropathic pain syndromes, "crosstalk" occurs between descending sympathetic nerves and ascending sensory nerves. Increases in sympathetic nervous system activity result in an increase of pain; this is known as sympathetically-mediated pain. Lesioning operations on the sympathetic branch of the autonomic nervous system are sometimes carried out. There are methods of treating sympathetically maintained pain in peripheral tissues. This is done topically to a patient having sympathetically maintained pain at a peripheral site where the pain originates. Wherein the sympathetically maintained pain can be diagnosed by local anesthetic blockade of the appropriate sympathetic ganglion or adrenergic receptor blockade via intravenous administration of phentolamine and rekindled by intradermal injection of norepinephrine.

Dietary supplements. There are two dietary supplements that have clinical evidence showing them to be effective treatments of diabetic neuropathy; alpha lipoic acid and benfotiamine. Administration of alpha lipoic acid (ALA) has been shown to reduce the various symptoms of peripheral diabetic neuropathy. While some studies on orally administered ALA had suggested a reduction in both the positive symptoms of diabetic neuropathy (including stabbing and burning pain) as well as neuropathic deficits (paresthesia), the metanalysis showed "more conflicting data whether it improves sensory symptoms or just neuropathic deficits alone." There is some limited evidence that ALA is also helpful in some other non-diabetic neuropathies.

Benfotiamine is a lipid-soluble form of thiamine that has several placebo-controlled double-blind trials proving efficacy in treating neuropathy and various other diabetic comorbidities.

D. Subjects

The methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

IV. Examples

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

In vitro selection and high-throughput sequencing and sequence specificity landscapes (SEQRS). SEQRS was conducted as described with minor modifications on PABPC162. The initial RNA library was generated from transcription of 1 μg of double-stranded DNA using the AmpliScribe T7-Flash Transcription Kit (Epicentre). DNA was removed through incubation with Turbo DNAse. Two hundred nangorams of RNA was added to 100 nM PABPC1 immobilized onto magnetic glutathione S-transferase (GST) resin (Fisher). Binding reactions were conducted in 100 μL of SEQRS buffer-50 mM HEPES, pH 7.4, 2 mM ethylenediaminetetraacetic acid (EDTA), 150 mM NaCl, 0.1% NP40, 1 mM dithiothreitol (DTT), 200 ng yeast transfer RNA (tRNA) competitor, and 0.1 U of RNase inhibitor (Promega). Magnesium and other metals catalyze non-specific cleavages in RNA; thus, a small amount of EDTA was included to enhance RNA integrity. An additional implication of EDTA in SEQRS is reduced preservation of structured RNAs throughout selection. Samples were incubated for 30 min at 22° C. prior to magnetic isolation of protein—RNA complexes. Unbound RNAs were aspirated and the beads were subjected to four washes with 200 μL of SEQRS buffer. After the final wash step, resin was suspended in elution buffer (1 mM Tris, pH 8.0) containing 10 pmol of the reverse transcription primer. Samples were heated to 65° C. for 10 min and then cooled on ice. Reverse transcription was conducted with ImProm-II reverse transcription reaction (Promega). The ssDNA product was used as a template for 25 cycles of PCR using a 50 μL GoTaq reaction (Promega). Sequencing data were processed as described (Lou et al., 2017). Sequence logos corresponding to consensus binding motifs were generated by weblogo from the top 300 most enriched sequences. To calculate the area under the curve, two likelihood distributions were used. The data were partitioned into test and training sets. The training sets were used to learn the data likelihood function. Using the learned likelihoods and the test dataset, the ROC was formed for each fold. Finally, the ROCs were averaged over the 10-folds. The total area under the curve was calculated based on a trapezoidal approximation. Frequency distributions of SEQRS sequences in CLIP data were determined based on histograms of cumulative distributions surrounding sites of productive crosslinking across the genome as described (Campbell et al., 2014).

Cell cultures. U2OS cell line cultures: The U2OS human osteosarcoma cell line was a gift from Dr. Shigeki Miyamoto (UW-Madison). Cells were cultured in high glucose Dulbecco's modified Eagle's Medium (DMEM, Corning) supplemented with 10% fetal bovine serum (FBS; Atlanta Biologicals). Cells were maintained at 37° C. in a humidified incubator with 5% $CO_2$.

DRG neuronal cell cultures: Tale Swiss Webster mice (Taconic laboratories, 15-25 g) were used. DRGs from all levels were excised aseptically and placed in Hanks' balanced salt solution (HBSS; Invitrogen) on ice. The ganglia were dissociated enzymatically with collagenase A (1 mg/mL, 25 min, Roche) and collagenase D (1 mg/mL, Roche) with papain (30 U/mL, Roche) for 20 min at 37° C. DRGs were then triturated in a 1:1 mixture of 1 mg/mL trypsin inhibitor (Roche) and bovine serum albumin (BioPharm Laboratories), then filtered through a 70 μm cell strainer (Corning). Cells were pelleted, then resuspended in DMEM/F12 with GlutaMAX (Thermo Fisher Scientific) containing 10% (Thermo Fisher Scientific), 1% penicillin and streptomycin, and 3 μg/mL 5-fluorouridine with 7 μg/mL uridine to inhibit mitosis of non-neuronal cells and were distributed evenly in poly-D-lysine-coated coverslips (BD Falcon) and incubated at 37° C. in a humidified 95% air/5% $CO_2$ incubator for 6 days.

Electrophoretic mobility shift. U2OS cell protein extracts of approximately 10 mg/mL were prepared with Ambion PARIS Kit (Thermo Fisher Scientific) according to the manufacturer's instructions. In brief, cells were washed once with cold phosphate-buffered saline (PBS), lysed in cell fractionation buffer, and incubated on ice for 10 min. Cytoplasmic lysate was collected after centrifugation for 5 min at 500×g. One microliter of 100 μM cyanine 3 phosphoramidite (Cy3)-labeled SPOT-ON was mixed with different amounts of protein lysate (0, 1, 2, 3, and 4 μL) in electrophoretic mobility shift assay (EMSA) buffer (10 mM HEPES, pH 7.4; 50 mM NaCl; 1 mM EDTA; 0.1 mg/mL bovine serum albumin; 0.01% (v/v) Tween-20, and 0.1 mg/mL yeast tRNA) and incubated on ice for 90 min. Three microliters of loading dye (15% (v/v) Ficoll 400 and 0.01% (v/v) bromophenol blue) was added to each 15 μL reaction before loading on the 6% DNA retardation gel (Invitrogen) in 0.5×TBE buffer at 100 V at 4° C. for 90 min. The gel was imaged with a Typhoon FLA7000 scanner (GE Healthcare).

RNA immunoprecipitation. U2OS cells were washed once with cold PBS and lysed in cold TNMEN-150 buffer (50 mM Tris, pH 8; 1 mM EDTA; 2 mM MgCl2; 150 mM NaCl and 0.5% (v/v) NP40) with 100 U/mL RNase inhibitor (Promega) and protease inhibitor (Roche). The cells were incubated on ice for 30 min, then centrifuged at a maximum speed for 10 min at 4° C. To generate PABP-depleted extracts, GST-tagged PAIP was purified in lysis buffer (50 mM Tris, pH 8; 500 mM NaCl; 0.1% (v/v) NP40; 1 mM $MgCl_2$; 1% glycerol; 5 mM DTT and supplemented with protease inhibitor). The protein lysate was incubated with glutathione agarose resin (Gold Biotechnology). One hundred microliters of aliquots of U2OS lysate was incubated at 4° C. for 1 h with GST-tagged PAIP which was already immobilized with glutathione agarose resin. Equal amounts of U2OS lysate was incubated with resin alone as a mock control. The lysate-resin mixture was centrifuged at 500 rpm for 5 min at 4° C. Supernatant was collected for the EMSA and RNA immunoprecipitation experiments. After PABP depletion, the supernatant was transferred to a new tube containing 15 μL of 100 μM biotin-labeled SPOT-ON and incubated on ice for 40 min. Twenty-five microliters of pre-equilibrated magnetic streptavidin beads (Pierce) were added to the SPOT-ON-biotin-lysate mixture and incubated for 80 min at 4° C. with continuous end-over-end rotation. Samples were then placed on a 96-well magnetic block and the beads were washed six times with cold wash buffer (50 mM Tris, pH 8; 1 mM EDTA; 2 mM $MgCl_2$; 150 mM NaCl and 0.05% (v/v) NP40). After the final wash step, beads were resuspended in 25 μL of 1× sodium dodecyl sulfate-polyacrylamide gel electrophoresis (SDS-PAGE) loading buffer and boiled for 5 min. Electrophoresis was conducted on 4-15% gradient SDS-PAGE gels (Bio-Rad) before transferring to nitrocellulose membrane. The membrane was probed with PABP antibody (1:500; Santa Cruz, sc-32318) followed by horseradish peroxidase-conjugated goat anti-mouse secondary antibody (1:300; Thermo Fisher Scientific, 32430). The signal was detected using ECL Select chemiluminescent substrate (GE Healthcare) on ChemiDoc Touch Imaging System (Bio-Rad).

Florescence polarization. Equilibrium dissociation constants were determined by florescence anisotropy measurements of either unmodified adenosine 12 nucleotide RNA or the Poly(A) SPOT-ON to recombinant human PABPC1 (residues 1-383). Binding reactions were conducted in 50 µL of buffer containing 50 mM HEPES, 5 mM EDTA, 250 mM KCl, 10 mM DTT, 0.5 mg/mL BSA, 0.05% Tween-20, 0.1 mg/mL yeast competitor total RNA (Ambion), and 0.5 nM Cy3-labeled RNA. Measurements were recorded on a Tecan Spark multimode plate reader in triplicate. Data were fit using Kalidagraph as described[63].

SPOT-ON stability. For U2OS cells, Cy3 3'-labeled SPOT-ONs were added respectively to DMEM media supplemented with 10% FBS and incubated at 37° C. at different time points (0, 0.5, 1, 2, 3, 6, and 24 h; unmodified Poly(A)12-Cy3 samples at 0, 12, 24, 36, and 48 h) were run on 6% DNA retardation gel in 0.5×TBE buffer. The gel was imaged with a Typhoon FLA7000 scanner (GE Healthcare).

SPOT-ON uptake. For U2OS cells, Cy3 3'-labeled SPOT-ONs were added to DMEM media supplemented with 10% FBS and incubated at 37° C. at different time points (0, 0.5, 1, 2, 3, 6, and 24 h). For DRG neurons, wells were incubated with Cy3 3'-labeled SPOT-ONs for 3 and 6 h. After SPOT-ON incubation, samples were processed for immunofluorescence.

Transient transfection. U2OS cells at 60-70% confluence were transfected with 0.5 g, 1, and 2 µg of pcDNA3.1-PABP or pcDNA3.1 empty vector, respectively, using Lipofectamine 3000 (Invitrogen) according to the manufacturer's instructions for 48 h. The cells were lysed and protein was extracted by ultrasonication in lysis buffer (50 mM Tris, pH 7.4, 150 mM NaCl, 1 mM EDTA, pH 8.0, and 1% Triton X-100) containing protease and phosphatase inhibitors (Sigma-Aldrich). Clear lysate was collected by centrifugation at 14,000×g for 20 min at 4° C. Protein samples in 1× Laemmli sample buffer (Sigma) was loaded and separated by 10% SDS-PAGE gels before transferring to Immobilon-P membranes (Millipore). The membrane was blocked in 5% milk for 1 h at room temperature, then incubated with PABP antibody (1:1000; cat. #ABE40, Millipore) overnight at 4° C. followed by goat anti-rabbit antibody conjugated to horseradish peroxidase (1:10,000; cat. #111-036-144, Jackson ImmunoResearch). The signal was detected using Pierce ECL Western Blotting Substrate (Thermo Fisher) on ChemiDoc Touch Imaging System (Bio-Rad). The blot was stripped in Restore Plus western blot stripping buffer (Thermo Fisher) according to the manufacturer's instructions and re-probed with c-Myc antibody (1:1000; cat. #MA1-980, Thermo Fisher) overnight followed by goat anti-mouse antibody conjugated to horseradish peroxidase (1:10,000; cat. #115-035-174, Jackson ImmunoResearch). After the signal was detected, the blot was stripped again and re-probed with glyceraldehyde 3-phosphate dehydrogenase (GAPDH) antibody (1:10,000; cat. #2118S, Cell Signaling) and goat anti-rabbit secondary antibody for GAPDH expression detection.

SUnSET and RPM assays. In the SUnSET assay (Schmidt et al., 2009), DRG neurons were cultured for 6 days in vitro. U2OS cells were plated on slides the day before the experiment to reach 70% confluence at the time of treatment. Test compounds (SPOT-ONs (10 µM) or homoharringtonine (50 µM)) were allowed to incubate for 37° C. for 3 h prior to the addition of puromycin (1 µM) for an additional 15 min. Immediately following the puromycin incubation, cells were washed in chilled HBSS containing 0.00036% digitonin (Sigma) for 2 min prior to fixation for the removal of background puromycin. In the RPM assay (Graber et al., 2013), cultures and treatments were conducted in an identical way to the aforementioned SUnSET assay. However, after incubation of test compounds, emetine (200 µM) was then added for 5 min and puromycin (100 µM) was added for an additional 5 min. Cells were washed with cold 0.00036% (v/v) digitonin prior to immunofluorescence.

Immunofluorescence. U2OS cell line cultures: Cells were fixed in 2% (v/v) formaldehyde (Thermo Fisher Scientific) in wash buffer (1% (v/v) BSA in PBS) at room temperature for 20 min. After washing three times with wash buffer, cells were permeabilized with 0.05% (v/v) saponin (Calbiochem) for 15 min, washed three times, and blocked in 10% (v/v) immunopure goat serum (MP Biomedicals) for 1 h. After three more washes, cells were stained with puromycin antibody (1:5000; Millipore, MABE343) and phalloidin-tetramethylrhodamine antibody (1:200; Sigma, P1951) at 4° C. overnight followed by goat anti-mouse antibody conjugated to Cyanine 5 (1:2000; Molecular Probe, A10524) at room temperature for 1 h. After three washes, cells were stained with 4',6-diamidino-2-phenylindole (285 nM) for 15 min and mounted with Prolong Diamond antifade mountant (Thermo Fisher Scientific).

DRG neuronal cell cultures: Cells were fixed in ice-cold 10% formalin in 1×PBS for 1 h. Cells were then washed with 1×PBS and permeabilized in PBS containing 10% heat-inactivated normal goat serum (NGS, Atlanta Biologicals, Atlanta, Ga., USA) and 0.02% Triton X-100 (Sigma) in 1×PBS for 30 min and then blocked in 10% NGS in PBS for at least 1 h. Following additional washes, primary antibodies were used to detect the following proteins: PABP1 (1:500; cat. #ABE40, Millipore), peripherin (1:1000; cat. #P5117 or cat. #SAB4502419, Sigma-Aldrich), and puromycin (1:5000; Millipore, MABE343). Primary antibodies were applied overnight at 4° C. and the next day appropriate secondary antibodies (Alexa Fluor, Invitrogen) were applied for 1 h. After additional PBS washes, coverslips were mounted on frosted slides with ProLong Gold antifade (Invitrogen).

In order to visualize the presence of PABP in growth cones, DRG neurons at day 4 in vitro were cultured, fixed, permeabilized, blocked, incubated, and mounted using similar conditions aforementioned. The presence of PABP in growth cones was identified using specific antibodies for β-III tubulin (1:1000, cat. #G712A, Promega), PABP1 (1:500; cat. #ABE40, Millipore), and peripherin (1:1000, cat. #CPCA-peri, EnCor Biotechnology).

Tissues: Mice were anesthetized with isoflurane and euthanized by decapitation and tissues were flash frozen in O.C.T. on dry ice. Spinal cords were pressure ejected using chilled 1×PBS. Sections of spinal cord (20 µm), DRG (20 µm), and sciatic nerve (20 µm) were mounted onto SuperFrost Plus slides (Thermo Fisher Scientific, Waltham, Mass., USA) and fixed in ice-cold 10% formalin in 1×PBS for 1 h and then subsequently washed three times for 5 min each in 1×PBS. Slides were then transferred to a solution for permeabilization made of 1×PBS with 0.2% Triton X-100 (Sigma-Aldrich). After 30 min, slides were washed three times for 5 min each in 1×PBS. Tissues were blocked for at least 2 h in 1×PBS and 10% heat inactivated NGS. Primary antibodies were used to detect the following proteins:

PABP1 (1:500; cat. #ABE40, Millipore), PABP4 (1:500; cat. #A301-467, Bethyl Laboratories), NeuN (1:1000; cat. #MAB377, Millipore), peripherin (1:1000; cat. #P5117 or cat. #SAB4502419, Sigma-Aldrich), TRPV1 (1:1000; GP14100, Neuromics), CD11b (1:1000; cat. #T-3102, BMA Biomedicals), and GFAP (1:1000; cat. #sc-33673, Santa Cruz Biotechnology). Primary antibodies were applied and incubated with spinal cord, DRG, and sciatic nerve sections on slides at 4° C. overnight. The next day, appropriate secondary antibodies (Alexa Fluor, Invitrogen) were applied for 1 h. After additional 1×PBS washes, coverslips were mounted on frosted slides with ProLong Gold antifade (Invitrogen). Cells or tissues from all groups were processed together under identical conditions with the same reagents and confocal microscopy images were obtained with an Olympus FluoView 1200 single-photon confocal microscope.

Image acquisition analysis. To calculate the puromycin incorporation and the distal ribopuromycilation, image analysis was performed using the ImageJ plug-in JACoP (Just Another Co-localization Plugin) (rsb.info.nih.gov/ij/plugins/track/jacop2.html)64. Manders' overlap coefficient M1 (peripherin/puromycin; using thresholds) was calculated in images collected from all groups. The M1 coefficient will vary from 0 to 1, the former corresponding to non-overlapping images and the latter reflecting 100% co-localization between both images. The M1 overlap coefficient values obtained from all groups were normalized to vehicle+puromycin group values and expressed as % of normalized puromycin incorporation.

To calculate the ribopuromycilation in proximal axons, the corrected total cell fluorescence (CTCF) was used to quantify the intensity of the puromycin signal for individual axons between experimental groups. In order to do so, an outline was drawn around the axons starting near to the cell bodies and extended up to 25 μm away from them. Using ImageJ, the integrated density and the area, as well as the background noise was measured and the CTCF calculated as equal to the integrated density−(area of selected cell×mean fluorescence of background readings). CTCF values from all groups were normalized to vehicle+puromycin group values and expressed as % of normalized proximal RPM.

To determine PABP immunoreactivity in either TRPV1-positive, CGRPpositive, and IB4-positive fibers or CD11b-positive and GFAP-positive cells, intensity correlation analysis (ICA) was calculated for regions of interest (ROI) in images (n=5 slices) collected from the L4-L6 region of the lumbar spinal dorsal horn. ICA computes the sum of (current pixel intensity in channel A−channel A's mean intensity)× (current pixel intensity in channel B−channel B's mean intensity) for each ROIs. Percentage of A channel over B channel intensity correlation is represented.

NGF and IL-6 models of hyperalgesic priming. A mouse model for "hyperalgesic priming" was used for the study. Animals were placed in acrylic boxes with wire mesh floors, and baseline plantar mechanical sensitivity was measured after habituation for 1 h using the up-down method 66. Briefly, Von Frey monofilaments (Stoelting, Wood Dale, Ill., USA) were firmly applied to the plantar surface of left hindpaw for 5 s and the up-down method was used to estimate the withdrawal threshold in grams (g). To establish hyperalgesic priming, the inventors co-administered the SPOT-ONs (0.3, 1 μg) with recombinant mouse IL-6 (1.25 ng; R&D Systems) or mouse 2.5S NGF (50 ng; Millipore) in 25 μL sterile PBS into the left hindpaw with an intraplantar (i.pl.) injection and measured their mechanical withdrawal thresholds at various time points after administration. Following complete resolution of the initial mechanical hypersensitivity (day 9), mice were again assessed for their mechanical withdrawal threshold and subsequently injected into the left hindpaw with PGE2 (100 ng; Cayman Chemical) in 25 μL sterile 0.9% NaCl. Afterwards, mechanical withdrawal thresholds were measured at 3 and 24 h post PGE2.

Plantar incision model. Prior to surgery all animals were assessed for baseline paw withdrawal thresholds using the up-down method. Baseline paw guarding, thermal, and grimace thresholds were assessed according to the methods described below. Plantar incision was performed as described previously[67]. A 5 mm longitudinal incision was made with a number 11 blade through skin, fascia, and muscle of the plantar aspect of the hindpaw in isoflurane-anesthetized mice. The skin was apposed with two sutures of 5 mm silk and immediately after mice received an intraplantar injection with SPOT-ONs in the incised paw and one more injection at 24 h in a total volume of 25 μL sterile PBS. Following complete resolution of the mechanical hypersensitivity (day 15), mice were administered PGE2 (100 ng; Cayman Chemical) into the plantar surface of the incised paw in a total volume of 25 μL.

MGS was used to quantify spontaneous pain in mice. The inventors scored the changes in the facial expressions at different time points after incision and after i.pl. PGE2 injection. In this method, all faces are to be coded for the presence and intensity of the following specific facial action units (AU): orbital tightening, nose bulge, cheek bulge, ear position, and whisker change. Intensity ratings are coded for each AU as follows: AU is not present=0, AU moderately visible=1, and AU severe=2. An MGS score for each mouse is calculated by averaging intensity ratings for each AU.

Paw guarding was quantified using a cumulative pain score in mice with minor modifications. Animals were placed in acrylic boxes with wire mesh floors and the incised hindpaw was closely observed during a 1-min period repeated every 5 min for 30 min. Depending on the position in which paw was found during the majority of the 1-min scoring period, a score of 0, 1, or 2 was given. Full weight bearing of the paw (score=0) was present if the wound was blanched or distorted by the mesh. If the paw was completely off the mesh, a score of 2 was recorded. If the area of the wound touched the mesh without blanching or distorting, a score of 1 was given. The sum of the six scores (0-12) obtained during the 30 min session was plotted.

Thermal changes of the incised hindpaw and non-incised hindpaw were visualized using a FLIR T31030sc thermal imaging camera (FLIR instruments). Animals were placed in acrylic boxes with wire mesh floors and imaged in baseline conditions and 24 h post incision. Image analysis of the medial plantar surface was performed using the FLIR ResearchIR Max 4 software.

Capsaicin-induced inflammatory pain model. Mice were habituated for 1 h to clear acrylic behavioral chambers before beginning the experiment. FLIR imaging and von Frey testing were performed using the methods described above. Thermal latency was measured using a Hargreaves device (IITC Life Science) with heated glass. Settings of 29° C. glass, 40% active laser power, and 20 s cut-off were used. CGRP receptor antagonist GGRP8-37 (1 μg, cat. #H-4924.0001, Bachem), scramble SPOT-ON (10 μg), or Poly(A) SPOT-ON (10 μg) were injected 15 min before intraplantar administration of 5 μg of capsaicin (cat. #M2028, Sigma). Mice were tested at 1, 3, and 24 h following intraplantar capsaicin administration. Drugs or capsaicin were injected with a volume of 10 μL via a 30.5-gauge needle. CGRP8-37, scrambled SPOT-ON, and Poly(A) SPOT-ON were diluted in 1×PBS. Capsaicin stock (1 mg/mL) was diluted in a solution 10% ethanol, 10% Tween-20, and 80% saline. At day 10, mice were assessed again before and after intraplantar injection of PGE2 (100 ng).

Animal usage. All procedures that involved use of animals were approved by the Institutional Animal Care and Use Committee of The University of Texas at Dallas and were in accordance with International Association for the Study of Pain guidelines. All behavioral studies were conducted using male Swiss Webster (Taconic Laboratories) mice weighing between 20 and 25 g. Animals were housed with a 12-h light/dark cycle and had food and water available ad libitum. The experimenters measuring mechanical withdrawal thresholds, paw guarding, and facial expressions were blinded to the experimental conditions. Mice were randomized to groups from multiple cages to avoid using mice from experimental groups that were cohabitating.

Transgenic mouse lines. To genetically label Schwann cells, mice that express Cre recombinase under the control of the myelin protein zero (MPz) gene were crossed with mice that have a loxP-flanked STOP fragment placed upstream of an enhanced green fluorescent protein fused to ribosomal protein unit L10a. Mice were purchased from the Jackson Laboratory. Statistical analysis. In vitro data were collected from three independent cell culture wells and are shown as means±s.d. or means±s.e.m. In vivo (behavior) data are shown as means±s.e.m. of six animals per group. Sample size was estimated as n=5 using G*power for a power calculation with 80% power, expectations of 50% effect size, with a set to 0.05. Graph plotting and statistical analysis used GraphPad Prism Version 7.0 (GraphPad Software). Statistical evaluation was performed by one-way or two-way analysis of variance, followed by post hoc Bonferroni test, and the a priori level of significance at 95% confidence level was considered at $P<0.05$. Student's t test was used to compare two independent groups. Specific statistical tests used are described in figure legends.

Example 2—Results

Unbiased analysis of PABP specificity. The inventors' experiments focus on the major cytoplasmic PABP isoform PABPC1 (henceforth referred to as PABP) as it is the most abundant isoform based on high-throughput sequencing of the dorsal root ganglia (DRG) (data not shown) (Gerhold et al., 2013). Furthermore, the inventors were unable to detect a clear signal of the second most abundant isoform in the DRG by immunofluorescence (data not shown). They examined the specificity of PABP for all possible 10-base sequences using in vitro selection, high-throughput sequencing of RNA, and sequence specificity landscapes (SEQRS; FIG. 1a). This versatile approach has been successfully applied to RNA-binding proteins that recognize structured or linear elements and protein complexes (Campbell et al., 2012; Campbell et al., 2014; Weidmann et al., 2016). PABP produced a highly reproducible pattern of enrichment (FIG. 1b). The most enriched sequence was an adenosine homopolymer. However, the diverse landscape of PABP that targets outside the Poly(A) tail suggests that interruptions in the Poly(A) sequence are tolerated in endogenous binding sites (Kini et al., 2016).

To determine if information obtained by SEQRS analysis of PABP in vitro values predicts the observed patterns of PABP occupancy in cultured mouse erythroleukemia cells, a model for PABP based on the top 50 8-mers was compared to a negative control with a similar compositional bias (FIG. 1c). The PABP model correctly identified genuine sites of occupancy in vivo (Wilcoxon-Mann-Whitney rank-sum test $P<0.003$). To estimate the sensitivity and specificity of the PABP model, the bound sequences were used to estimate the area under the receiver operated curve (AU-ROC; FIG. 1d). The model performs well at discriminating between true positives relative to false positives (AU-ROC=0.81). The repertoire of preferable PABP recognition sequences is apparent based on alignment of the top 300 10-mers which indicate a strong preference for A throughout the motif with a bias towards U followed by G at the first 9 positions (FIG. 1e). Position 10 has a slight preference for G over U. Based on these comprehensive measurements, the inventors conclude that PABP is highly specific for sequences that are rich in adenosine with a preference toward adenosine homopolymers—a result consistent with known regulatory functions on the Poly(A) tail and elsewhere (Burgess & Gra, 2010; Kahvejian et al., 2001; Mangus et al., 2003; Gorgoni et al., 2011; Sachs, A., 2000).

Design of a novel PABP inhibitor. As a novel means of competitively inhibiting PABP function, the inventors applied their unbiased assessment of PABP specificity toward the development of specificity-derived competitive inhibitor oligonucleotides (SPOT-ON). They modified RNAs that are designed to bind to PABP in order to stabilize them in two key ways. First, to reduce the ability of the 2' ribose hydroxyl to catalyze intramolecular cleavage, the inventors incorporated 2' O-methyl ribose modifications throughout the RNA (Hernandez et al., 2012). Second, to reduce the activity of exonucleases in either direction, the 5' and 3' most base in the phosphodiester linkage was replaced with sulfur giving rise to terminal phosphorothioate bonds (Ciafre et al., 1995). A minimum of 11-12 adenosines are required for high affinity binding to PABP (Deo et al., 1999) Therefore, a compact 12 base RNA termed the Poly(A) SPOT-ON was generated as a potential competitive inhibitor with the composition A*AAAAAAAAAA*A (where * denotes phosphorothioate linkages) (SEQ ID NO: 3). The Poly(A) SPOT-ON mimics the composition of the Poly(A) tail. As a key negative control, the inventors used a random sequence with identical chemical configuration as before and designate this RNA as the scramble SPOT-ON (U*AACAAAAUAA*U) (SEQ ID NO: 4).

Figure 2:
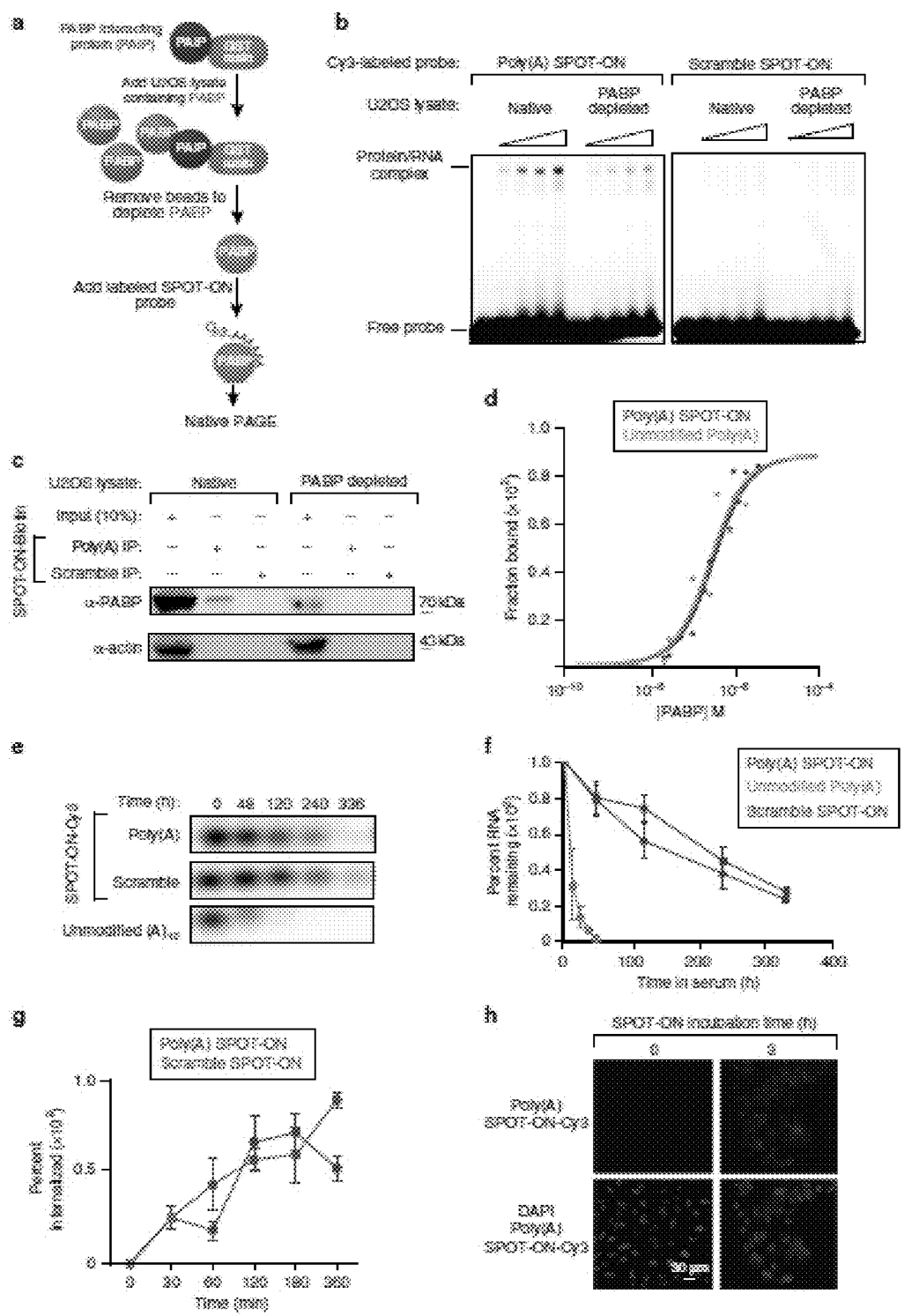
FIGS. 2A-H. Characterization of the in vitro binding specificity of the Poly(A) SPOT-ON and cellular uptake.

The inventors examined if the Poly(A) SPOT-ON binds to PABP in a series of in vitro experiments. In the first series of experiments, two extracts were prepared. They made use of an established protocol for efficient depletion of PABP by pre-incubation with immobilized PABP-interacting protein (PAIP) (FIG. 2a) (Svitkin & Sonenberg, 2004). As a negative control, a second extract containing PABP was mock depleted in parallel. Each lysate was incubated with either the Poly(A) SPOT-ON or the scramble SPOT-ON and subjected to native electrophoresis (FIG. 2b). The inventors found a single clear band present in the Poly(A) SPOT-ON sample which is greatly reduced in intensity following PABP depletion (53%). Importantly, the negative control lacked clear binding to any species present in the whole cell extract. As an additional test for specificity, the SPOTONs were generated with 3' biotin labels and again incubated with whole cell lysate. After allowing binding to proceed and performing numerous wash steps, the inventors probed input and IP samples with antibodies for either PABP or actin (FIG. 2c). They found evidence for specific binding between the Poly(A) SPOTON which was diminished in PABP-depleted samples. Finally, equilibrium dissociation constants were determined by florescence polarization for PABP bound to either an unmodified 12-base Poly(A) sequence or the Poly(A) SPOT-ON (FIG. 2d). Nonlinear least-squares regression analysis yielded Kd values of 261±54 and 301±41 nM for the unmodified or Poly(A) SPOT-ON, respectively. These results collectively argue that the Poly (A) SPOT-ON interacts with PABP with a high degree of specificity in vitro.

The stability of the SPOT-ONs was compared to unmodified RNA to determine if the modifications to the SPOT-ON enhanced stability. Indeed, the half-life of the unmodified RNA was approximately 18 h (FIGS. 2e, f). Comparable measurements of the SPOT-ON indicate half-lives of >10 days. The inventors also examined the cellular uptake of the SPOT-ONs in U2OS cells (FIG. 2g). The SPOT-ONs are efficiently taken up and are distributed throughout the U2OS cells after a 3-h period (FIG. 2h; data not shown).

Figure 3:
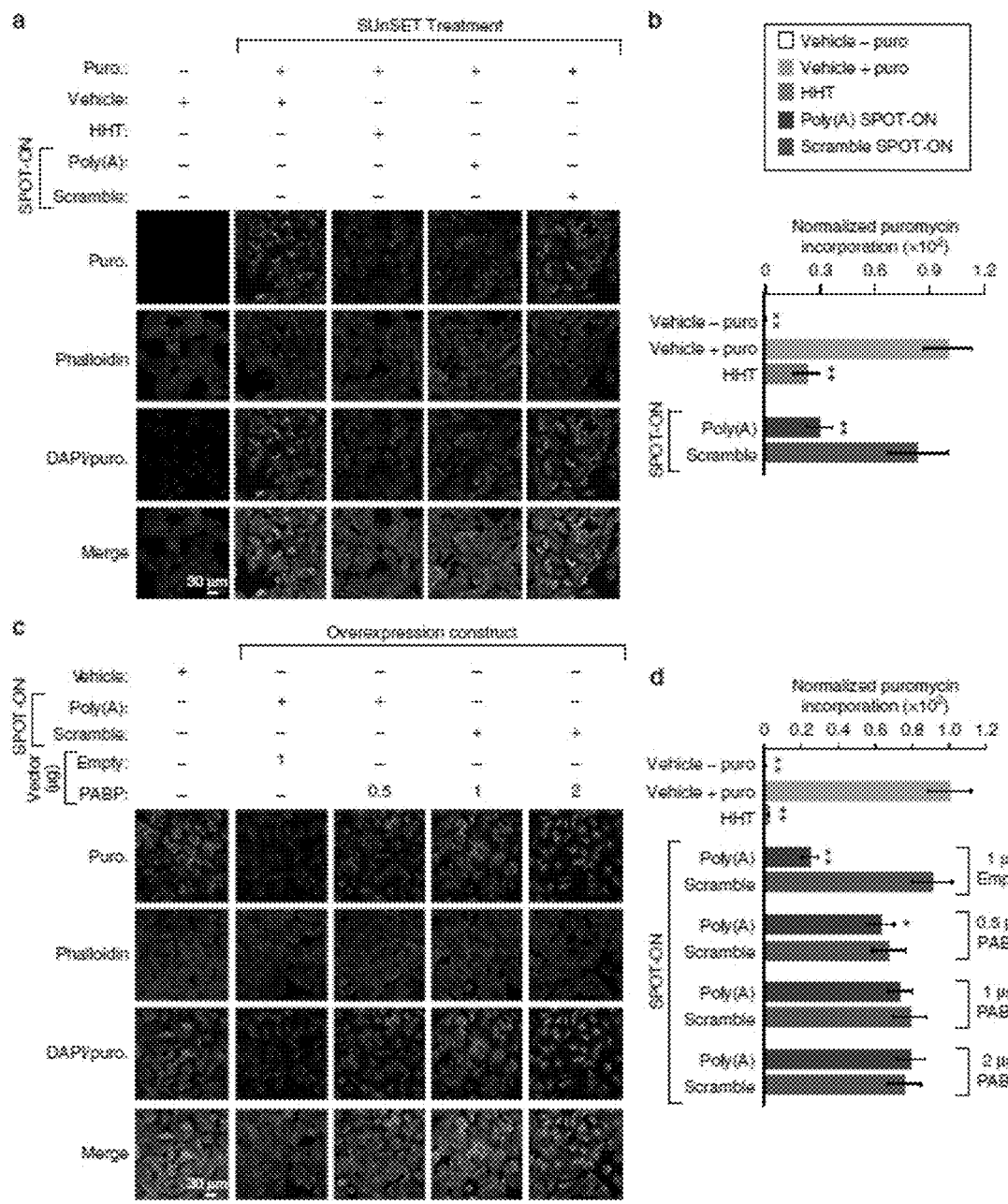
FIGS. 3A-D. The Poly(A) SPOT-ON attenuates nascent protein synthesis.

The Poly(A) SPOT-ON reduces translation. Using the nonradiometric surface sensing of translation Surface Sensing of Translation (SUnSET) approach, the inventors measured nascent protein synthesis levels in U2OS cells (FIGS. 3a, b) (Schmidt et al., 2009). In this method, the structural analog of an aminoacyl-transfer RNA, puromycin, is used because it is readily incorporated into elongating polypeptides (Nathans, D., 1964). This causes termination of peptide elongation and release of the nascent peptide. The levels of puromycin can be visualized using a highly specific monoclonal antibody. In the inventors' experiments, they used a cytoskeletal marker for filamentous actin, phalloidin, as an internal control for differences in the number of cells in each image. As a key negative control, they excluded puromycin and observed little background signal. Inclusion of puromycin resulted in robust levels of translation. However, introduction of either homoharringtonine, an inhibitor of elongation, or the Poly(A) SPOT-ON reduced nascent protein synthesis by 77.6% and 70.4%, respectively (F4, 72=254, P<0.0001; FIG. 3b). The scrambled SPOT-ON did not produce a significant effect.

To determine if the reduction in protein synthesis was due to inhibition of PABP, the inventors transfected either an empty overexpression vector, pCDNA3, or a vector encoding full-length PABP (FIGS. 3c, d). PABP expression was confirmed by immunoblotting (data not shown). The inventors found that the robust inhibition of protein synthesis caused by the Poly(A) SPOT-ON was ameliorated by PABP overexpression with the largest effects seen at high vector concentrations (F10, 63=180.1, P<0.0001; FIG. 3d). Thus, PABP expression significantly increased protein synthesis in the presence of the Poly(A) SPOT-ON. Addition of transfection reagents nonspecifically reduced protein synthesis by 10-20%. These changes are consistent but not significant relative to the untreated positive control. Following overexpression of PABP, the amount of nascent protein synthesis observed for the scramble and Poly(A) SPOT-ON is indistinguishable. This suggests strongly that PABP is the relevant cellular target of the SPOT-ON.

The Poly(A) SPOT-ON impairs initiation. To further characterize the mechanism of action of the Poly(A) SPOT-ON, the inventors made use of a modified version of SUnSET termed ribopuromycylation (RPM) to assay ribosome runoff (David et al., 2011; 2012; Willett et al., 2011; Graber et al., 2013). Unlike SUn-SET, cells are incubated with an irreversible inhibitor of elongation (emetine) and thus nascent chains are unable to dissociate from the ribosome and re-initiation is inhibited. Puromycylated proteins do not accumulate in monosomal fractions and sediment exclusively with heavy polysomes (David et al., 2012). Thus, only a single round of translation is assayed through the use of puromycin immunofluorescence and normalized as before. The inventors used this approach to differentiate what step in protein synthesis is impacted by the Poly(A) SPOT-ON through order of addition experiments.

Figure 4:
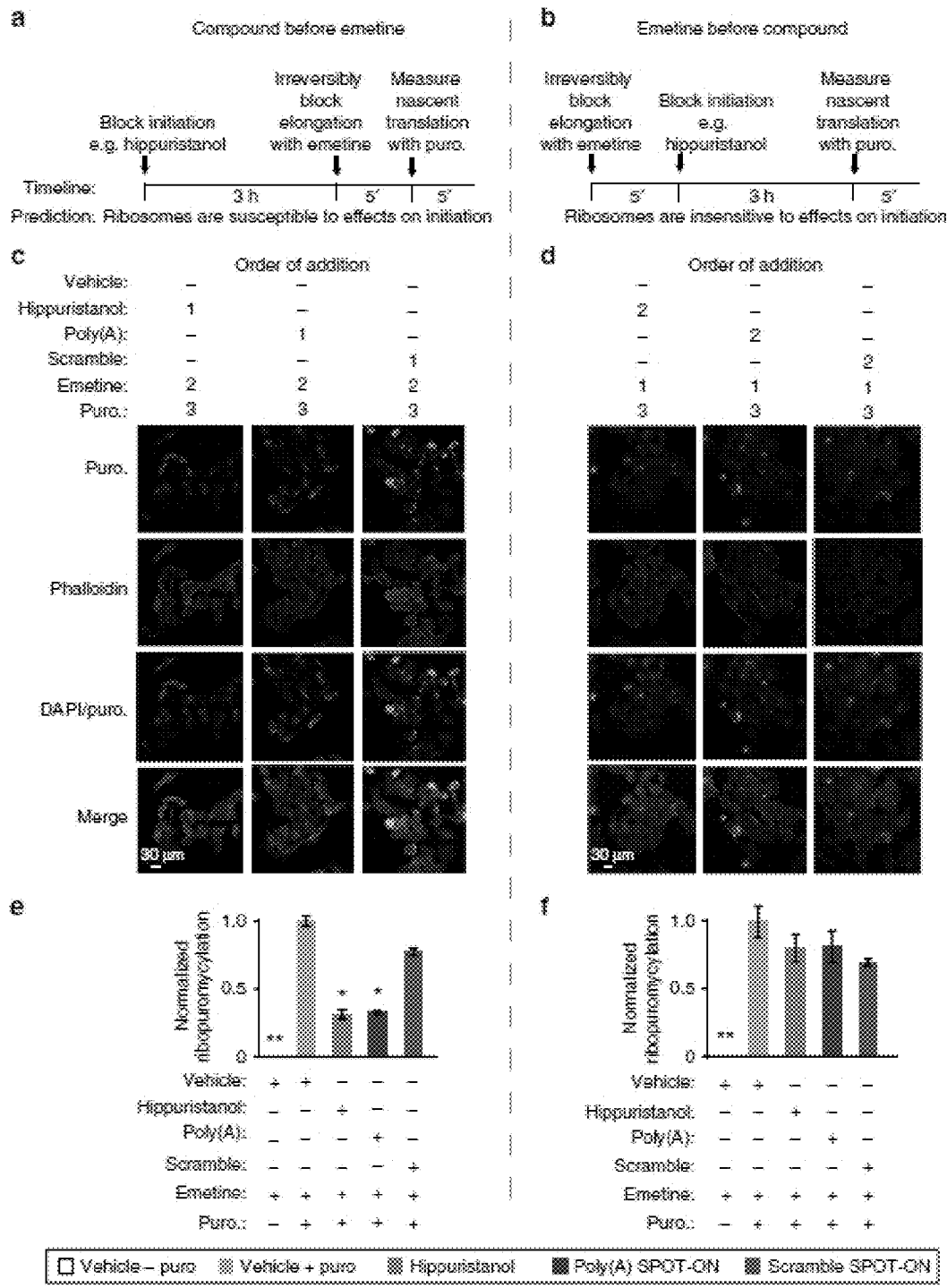
FIGS. 4A-F. The Poly(A) SPOT-ON acts on initiation phase of protein synthesis.

The inventors examined the effects of the eIF4A inhibitor hippuristanol as a key positive control for disruption of initiation of protein synthesis (FIGS. 4a, b). They reasoned that by disrupting initiation prior to elongation, the final availability of ribosomes should reflect differences in initiation efficiencies. They added either hippuristanol, the Poly (A) SPOT-ON, or the scramble SPOT-ON prior to blocking elongation irreversibly with emetine and labeling ribosome-associated polypeptide chains with puromycin. The inventors found that addition of either hippuristanol or the Poly (A) SPOT-ON significantly reduced RPM staining, whereas a vehicle or scramble SPOT-ON treatment did not (F4, 19=157.2, P<0.0001; FIGS. 4c, e). In reciprocal experiments, they predicted that irreversible blockade of elongation would mask the effects of compounds that reduce initiation as the majority of ribosomes would be trapped in the elongation phase of translation. Significant changes were absent between samples containing inhibitors of any type or negative controls (vehicle and scramble SPOT-ON; FIGS. 4b, d, f). The inventors conclude that the Poly(A) SPOT-ON likely impairs initiation consistent with the known role of PABP in stimulating cap-dependent translation via eIF4G (Gallie, D. R., 1991; Tarun & Sachs, 1996; Le et al., 1997; Imataka et al., 1998).

Figure 5:
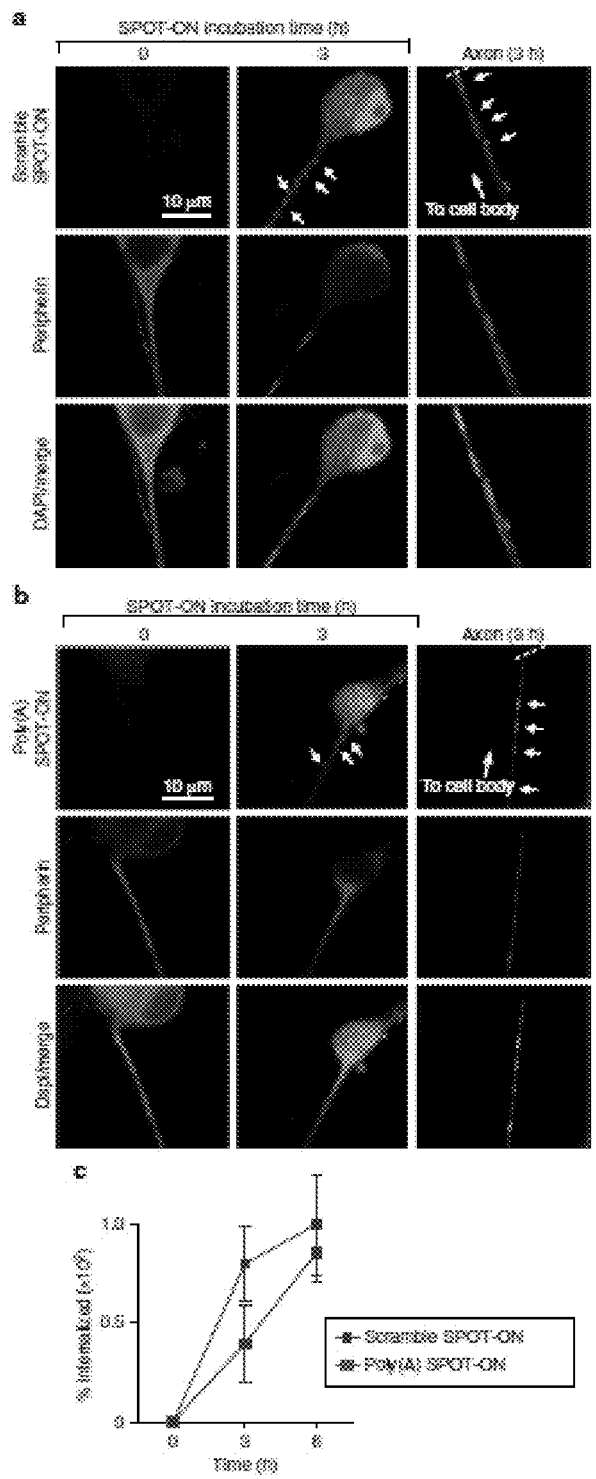
FIGS. 5A-C. SPOT-ONs are taken up by cultured DRG sensory neurons. Uptake of SPOT-ONs was determined based on imaging of cultured DRG neurons over time.
Figure 6:
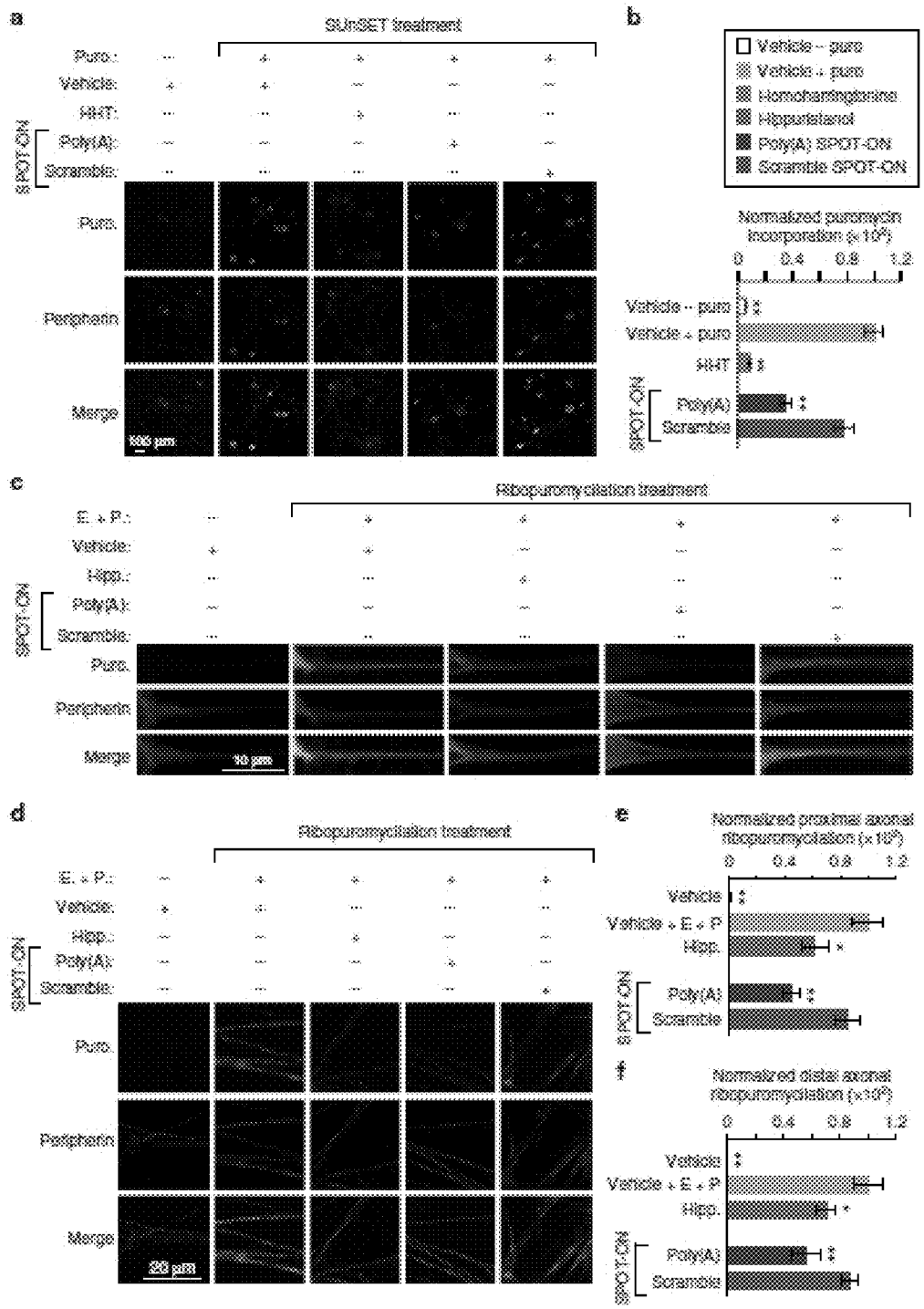
FIGS. 6A-F. The Poly(A) SPOT-ON reduces nascent protein synthesis and axonal translation in DRG neurons.

Translation in sensory neurons. First, the inventors demonstrated that the SPOT-ONs are efficiently taken up and are distributed throughout the soma of DRG neurons including localization into their axons after a 3-h period (FIGS. 5a-c). Second, to probe if sensory neurons responded to PABP inhibition in a similar way to cell lines, the inventors determined rates of nascent protein synthesis in mouse DRG sensory neurons using SUnSET (FIGS. 6a, b). To specifically mark neurons that are likely nociceptors, they scored only peripherin-positive cells. Robust translation was observed in the presence of puromycin (vehicle). Addition of either the general protein synthesis inhibitor homoharrintonine or the Poly(A) SPOT-ON significantly reduced protein synthesis (F4, 26=13.47, P<0.0001; FIG. 6b). The scramble SPOT-ON failed to produce a significant effect. These results argue that the inhibitory effects of the SPOT-ONs are consistent between primary mouse neurons and the inventors' immortalized cell line.

Localized translation is fundamental to neuronal plasticity and has been linked to pain plasticity (Price & Geranton, 2009). To ascertain if the SPOT-ON impairs axonal translation, the inventors again utilized RPM to quantify protein synthesis levels in axons either proximal to the cell body or at distal regions in the presence or absence of the Poly(A) SPOT-ON (FIGS. 6c, f). DRG neurons were treated with either hippuristanol, the Poly(A) SPOT-ON, or the scramble SPOT-ON. The inventors found that addition of either hippuristanol or the Poly(A) SPOT-ON, but not scramble SPOT-ON or vehicle, significantly reduced proximal (F4, 93=10.63, P<0.0001; FIG. 6c, e) and distal (F4, 39=19.34, P<0.0001; FIGS. 6d, f) axonal RPM staining in DRG sensory neurons. The RPM signal originating from distal axons is more diffuse than the punctate signal observed in dendrites from primary rat hippocampal neurons (Graber et al., 2013). This may reflect experimental differences such as bona fide organizational changes in subcellular distribution of ribosomes. These results from nociceptor axons are consistent with prior work suggesting that ribosomes in myelinated axons of lumbar spinal nerve roots are arranged in periaxoplasmic plaques (Koenig et al., 2000).

Figure 7:
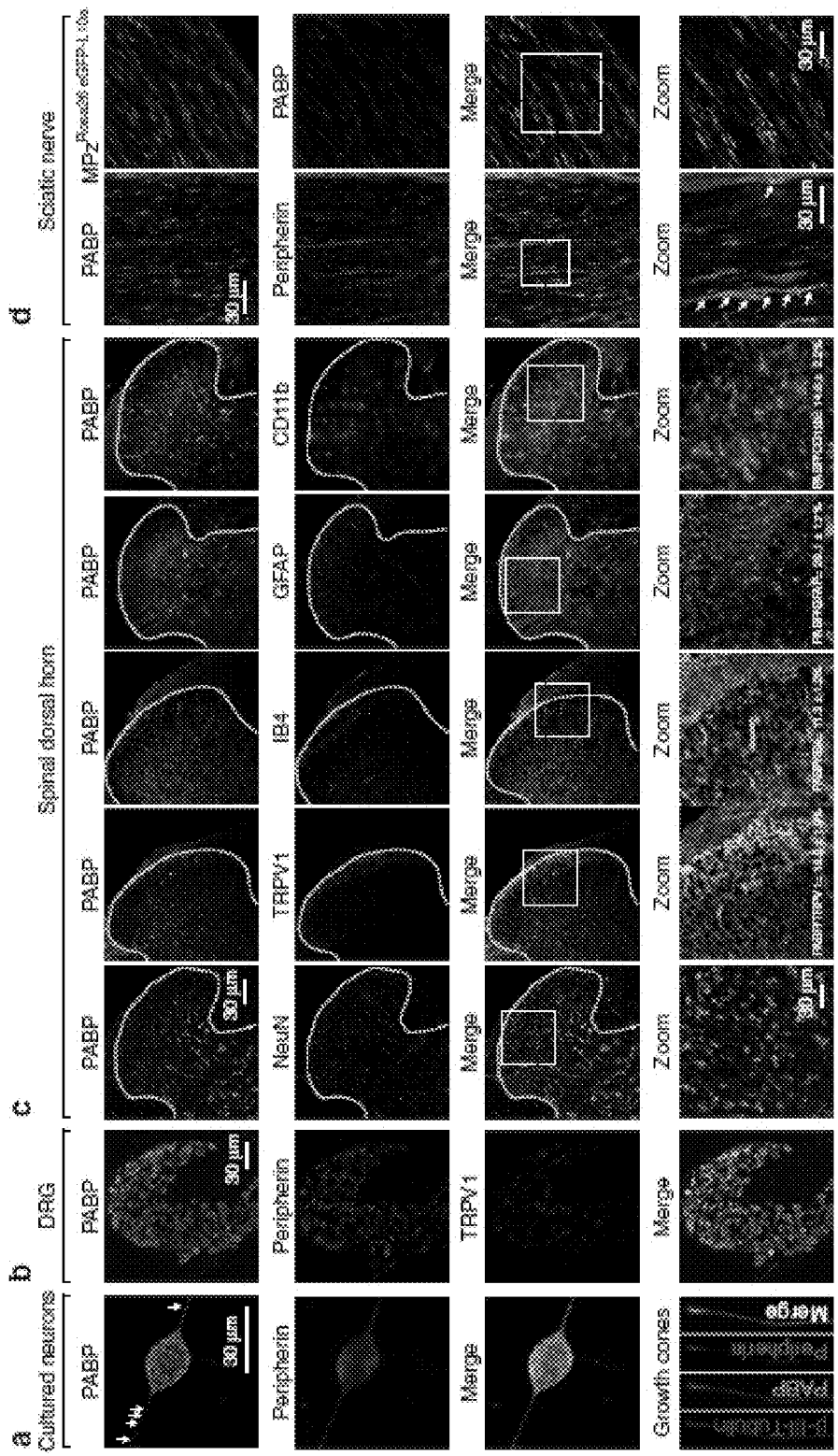
FIGS. 7A-D. Binding protein PABP is present throughout the peripheral nervous system.

PABP distribution in the peripheral nervous system. To characterize the cellular distribution of PABP in the primary nociceptive system, the inventors used immunohistochemistry (FIGS. 7a-d). PABP was expressed in the soma of cultured DRG sensory neurons with high levels of PABP localizing into the axons (FIG. 7a). Next, the DRG (FIG. 7b), spinal dorsal horn (FIG. 7c), and sciatic nerve (FIG. 7d) were examined. Consistently with the expression in cultured DRG neurons, they found that PABP was broadly expressed and co-localized with peripherin immunoreactivity, a marker for unmyelinated, mostly nociceptive neurons. They also found that PABP was expressed in transient receptor potential cation channel subfamily V member 1 (TRPV1)-positive neurons in the DRG, indicating its presence in small-diameter, unmyelinated C-fibers and medium diameter, thinly myelinated A6 fibers. In the spinal cord dorsal horn, PABP is present in neurons as evidenced by co-localization with the neuronal marker NeuN.

Moreover, PABP was differentially observed in isolectin B4 (IB4)-immunoreactive and TRPV1-immunoreactive fibers in the superficial layers of the dorsal horn. These results indicate that PABP is localized within pre-synaptic central terminals of nociceptive DRG neurons. Although PABP is present in nociceptive neurons suggesting a key role in axonal translation, it is also found in non-neuronal cells such as microglia and astrocytes in the spinal dorsal horn. Furthermore, PABP is located in the axons of the sciatic nerve in tissues as well as in cultured nociceptors. Consistent with the presence in nonneuronal cells in the spinal cord, PABP is also present in Schwann cells in the sciatic nerve as revealed by the co-localization with the myelin protein zero (MPz) protein. Together, this suggests that PABP might serve critical but unexplored roles in nociception, including regulating translation at the distal ends of nociceptors in the periphery and spinal dorsal horn.

Inhibition of NGF- and IL-6-mediated allodynia. A standard method to evaluate allodynia in mice and humans is measuring mechanical sensitivity in response to von Frey filament application. Under normal conditions (no pain), plantar mechanical withdrawal threshold in mice is approximately 1.0-1.5 g force. However, after intraplantar injection of pro-inflammatory mediators or tissue injury, nociceptors become sensitive to mechanical stimulation. A drop or increase in the withdrawal threshold after insult is interpreted as hyperalgesia and analgesia, respectively. Commonly, NGF and IL-6 are used as pro-inflammatory mediators; both increase nociceptor excitability and induce plasticity, resulting in mechanical hypersensitivity (Melemedjian et al., 2010). After the resolution of the initial insult produced by NGF or IL-6, a long-lasting sensitivity to subsequent stimulation by the inflammatory mediator prostaglandin E2 (PGE2) is observed. PGE2 is commonly used as a mild stimulus that produces a short-term hypersensitivity in naïve animals. However, when animals are previously primed with noxious stimuli, PGE2 is now capable to produce a longlasting hypersentivity. This event is referred to as hyperalgesic priming and is frequently associated with the process underlying the transition from acute to chronic pain (Reichling & Levine, 2009). The inventors examined if the Poly(A) SPOT-ON impairs NGF-induced or IL-6-induced changes in mechanical hypersensitivity in vivo. They also assessed the presence of hyperalgesic priming in all groups 9 days after NGF or IL-6 treatment, a time point where animals had completely returned to baseline mechanical thresholds, by giving an intraplantar injection of PGE2. They did not observe any changes in NGF-induced mechanical hypersensitivity in the presence of vehicle or scramble SPOT-ON (FIG. 8a) or after precipitation of priming with PGE2 (FIG. 8b). However, the highest dose of Poly (A) SPOT-ON markedly inhibited NGF-induced mechanical hypersensitivity (F2, 90=26.59, P<0.0001; FIG. 8c) and blocked the development of hyperalgesic priming (F2, 45=22.14, P<0.0001; FIG. 8d). Likewise, IL-6-induced mechanical hypersensitivity and priming was not affected by vehicle or scramble SPOTON administration (FIGS. 8e, f), but the Poly(A) SPOT-ON efficiently reduced mechanical hypersensitivity (F2, 72=15.13, P<0.0001; FIG. 8g) and the development of hyperalgesic priming (F2, 42=9.935, P=0.0003; FIG. 8h). These results suggest that the Poly (A) SPOT-ON blocks produce pain sensitization driven by NGF and IL-6 and the development of hyperalgesic priming.

Figure 8:
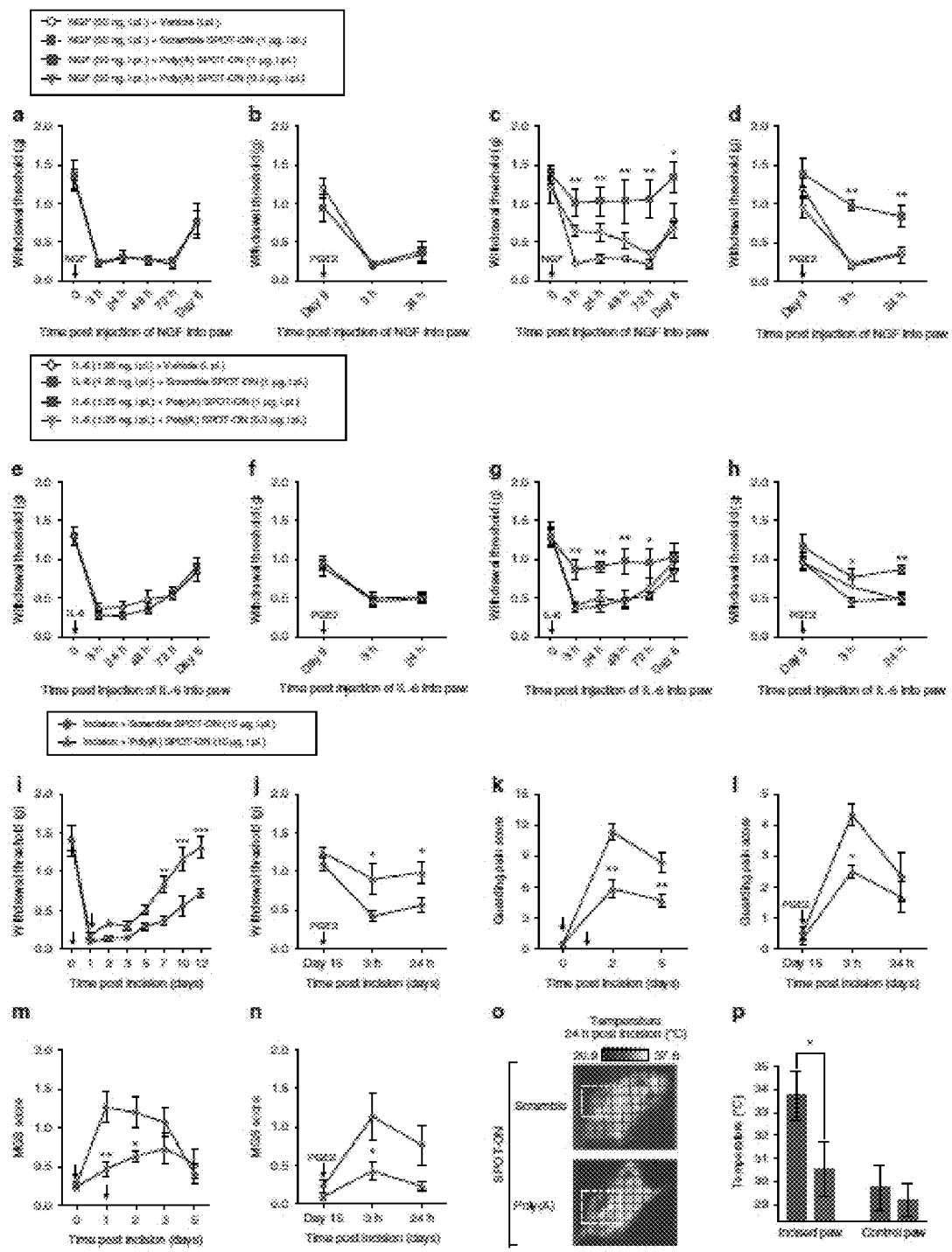

Incision-evoked pain responses. Both NGF and IL-6 are locally produced following tissue injury, including incision for surgery, where they are involved in producing prolonged hyperexcitability that promotes peripheral sensitization in nociceptors that innervate the injured area (Banik et al., 2005; Spofford & Brennan, 2012). The inventors tested whether the Poly(A) SPOTON would also inhibit incision-evoked pain in mice. They again assessed the presence of hyperalgesic priming in all groups 15 days after surgery when the animals had returned to baseline mechanical thresholds. Local injection at the time of incision and injection at the incision site 24 h after surgery with the Poly(A) SPOT-ON, but not scramble SPOT-ON, decreased incision evoked mechanical hypersensitivity and contributed to the more rapid resolution of mechanical pain sensitization (F1, 80=37.44, P<0.0001; FIG. 8i). Injection of the Poly(A) SPOT-ON also blocked the development of hyperalgesic priming produced by incision (F1, 30=13.57, P=0.0009; FIG. 8j). In the same animals, the inventors tested whether the Poly(A) SPOT-ON had an effect on incision-induced spontaneous pain responses. No paw guarding behavior was observed before plantar incision. However, robust paw guarding behavior was present in the incised paw following surgery and after demonstration of priming with PGE2 (FIG. 8,1). Local injection of the Poly(A) SPOT-ON, but not the scramble SPOTON, significantly reduced the development of paw guarding following surgery (F1, 30=28.7; P<0.0001; FIG. 8k) as well as when the animals were subsequently challenged with PGE2 15 days after incision (F1, 30=6.214, P=0.0184; FIG. 8l). Using the same protocol, the inventors recorded the affective component of pain by scoring the facial expressions of the animals before and after surgery based on facial cues. In this model, an increase in the Mouse Grimace Scale (MGS) was observed following surgery and after demonstration of priming with PGE2 (FIGS. 8m, n). Local injection of the Poly(A) SPOT-ON, but not the scramble SPOTON, significantly reduced the development of facial grimace following surgery (F1, 50=12.03, P=0.0011; FIG. 8m) and 3 h after hyperalgesic priming revealed by PGE2 injection (F1, 30=10.44, P=0.0030; FIG. 8n). Finally, the inventors determine the thermal changes in the incised vs. non-incised paw as an indirect measure of inflammation using a similar approach previously reported for inflammatory and arthritic pain models (Sanchez et al., 2008). They reasoned that proinflammatory mediators released at the site of surgery produce inflammation and, at the same time, an increase in paw temperature due to enhanced blood flow. Incised paws displayed increased temperature 24 h after surgery (FIGS. 8o, p). The inventors did not observe any thermal changes in the non-incised paw after surgery, indicating that pro-inflammatory mediators are released only in the inflamed area. Local administration of the Poly(A) SPOT-ON, but not the scramble SPOT-ON, significantly decreased the incised paw temperature when mice were assessed 24 h after surgery (t=2.795, P=0.0209; FIGS. 8o, p). Taken together, these results indicate that local treatment with the Poly(A) SPOT-ON can be a potentially efficacious treatment for the prevention of pain and inflammation brought about by tissue injury.

Figure 9:
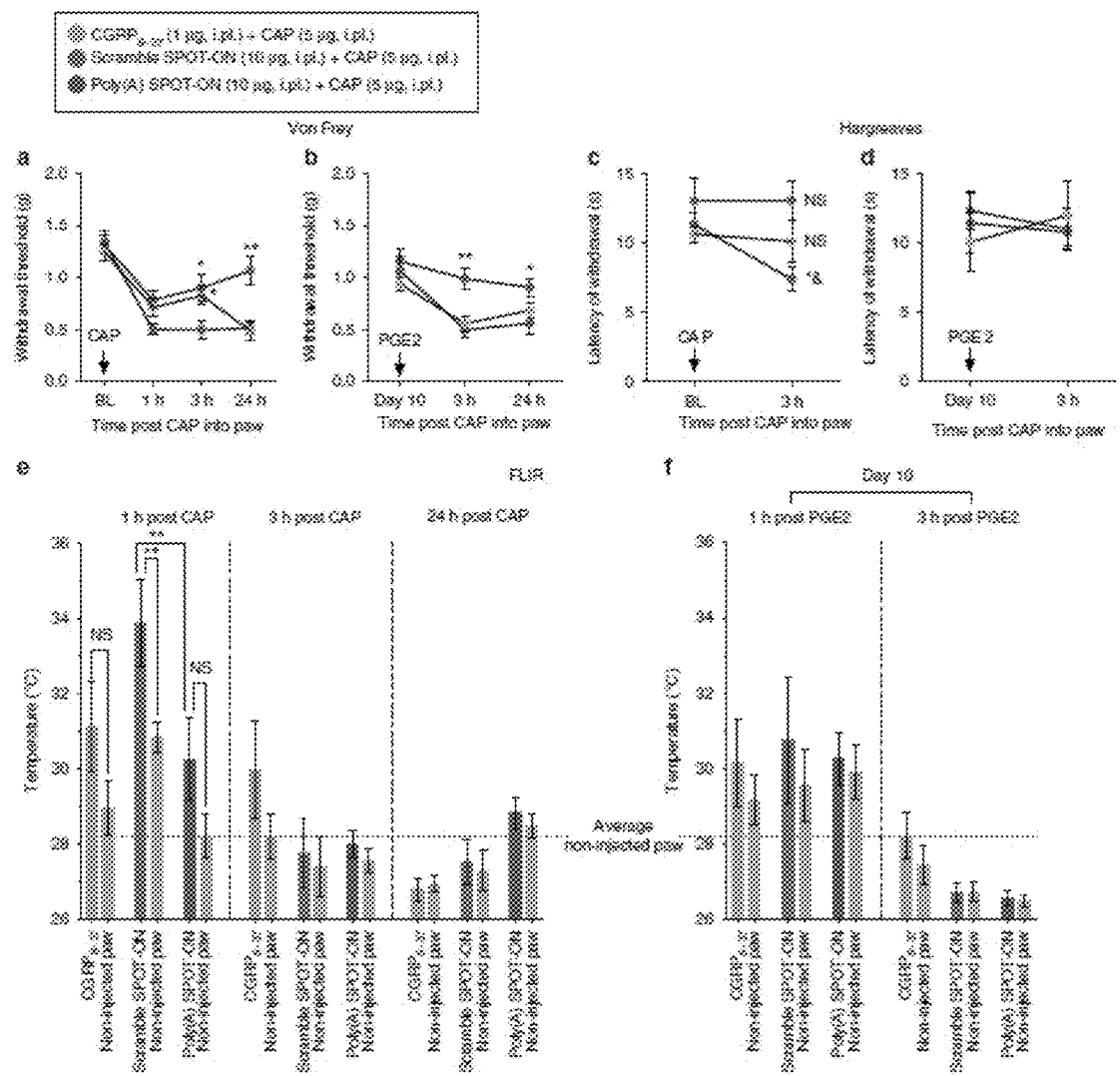
FIGS. 9A-F. The Poly(A) SPOT-ON reduces pain sensitization produced by capsaicin.

Capsaicin-induced inflammatory pain. Neurogenic inflammation plays a key role in nociceptor sensitization by a mechanism that is partially driven by the neuropeptide release, such as CGRP, from primary afferent fibers in response to noxious stimuli including capsaicin, an agonist of TRPV1 channels (Richardson et al., 2002). In order to show more evidence that nociceptors are relevant targets of the Poly(A) SPOT-ON, the inventors used capsaicin as an inflammatory mediator because of its very specific interaction with nociceptors. This idea was justified based on the results showing the presence of PABP in TRPV1-positive neurons in the DRG and pre-synaptic endings in the spinal dorsal horn (FIGS. 7b, c). Intraplantar injection of capsaicin produced mechanical and thermal hypersensitivity together with a transient increase in paw temperature (FIG. 9). The Poly(A) SPOT-ON, but not the scramble SPOT-ON, inhibited capsaicin-induced mechanical hypersensitivity (F2, 56=11.06, P<0.0001; FIG. 9a) and blocked the development of hyperalgesic priming (F2, 45=9.801, P=0.0003; FIG. 9b). Moreover, CGRP8-37, a CGRP receptor antagonist, had a transient antinociceptive effect at 3 h post capsaicin administration and did not block the precipitation of hyperalgesic priming at day 10 (FIGS. 9a, b). Similarly, development of thermal hypersensitivity was attenuated by the Poly(A) SPOT-ON and CGRP8-37 with no significant antinociceptive effects observed in the scramble SPOT-ON group (F2, 30=4.972, P=0.0137; FIG. 9c). However, no changes in thermal hypersensitivity were detected in any groups after priming revealed by PGE2 injection (FIG. 9d). Coupling thermal hypersensitivity with forward looking infrared (FLIR) imaging, the inventors observed that the Poly(A) SPOT-ON and CGRP8-37, but not the scramble SPOTON, blocked the transient increase in paw temperature produced by intraplantar capsaicin administration (F5, 30=4.741, P=0.0026; FIG. 9e). Similar to the thermal hypersensitivity data, no changes in capsaicin-injected paws compared to non-injected paws were detected with FLIR after priming revealed by PGE2 (FIG. 9f). Together, these results demonstrate that part of the effect produced by the Poly(A) SPOT-ON is mediated by blocking induction of axonal plasticity in primary afferent fibers responsive to capsaicin.

Example 3—Discussion

These experiments permit four major conclusions. First, RNA-based SPOT-ON "decoys" can inhibit RNA-protein interactions and are functional in vivo. Second, PABPs are broadly distributed in the nociceptive pathway and play critical roles in protein synthesis. Third, inhibition of PABPs with SPOT-ONs can robustly impair pain behavior. Fourth and finally, PABP inhibition diminishes inflammation following incision or intraplantar capsaicin administration.

The inventors determined the sequence preferences of a conserved translation factor and applied this information toward the generation of a competitive inhibitor RNA. This constitutes, to the best of the inventors' knowledge, the first such attempt to disrupt RNA-protein interactions through the use of chemically-stabilized mimetics. This approach is particularly well suited to PABPs given their essential requirement in basal eukaryotes such as yeast and in animals. SPOT-ONs are rapidly taken up by cells and lack overt signs of toxicity. The SPOT-ONs the inventors report are not tailored for uptake by a specific cell type and could be improved upon through targeting moieties for nociceptor neurons. Similar approaches devised to improve delivery of microRNA antagonists could in principle improve the potency of SPOT-ONs in vivo (Li & Rana, 2014).

The implications of this approach are broad given the function of the Poly(A) SPOT-ON in vivo and the need to understand the function of the more than 800 RNA-binding proteins found in the human genome (Castello et al., 2012). The modifications introduced into the SPOT-ON were well tolerated by PABP; the Poly(A) SPOT-ON binds with comparable affinity to an unmodified substrate and appears to be highly specific in gel-shift and cell-based measurements. PABP is abundant in the cell and has a moderate affinity for Poly(A) RNA. The inventors' ability to competitively inhibit its function bodes well for RNA-binding proteins as a class given that many recognize more complex elements with higher affinity. This approach may broadly provide a means to interrogate the function of RNA-binding proteins whose specificity is distinct through the use of similar RNA-derived decoys.

PABPs are present in the peripheral nervous system. While abundant in the somas of DRG neurons, they are also clearly present in axons. This contributes to a growing body of evidence in support of PABP as an active participant in RNA localization and in localized translation. For instance, PABP is present in dendrites and terminal growth cones and binds to localized regulatory RNAs including BC1 and BC200 (Muddhashetty et al., 2002; Zhang et al., 2007). PABP physically associates with proteins that modulate local protein synthesis in dendrites such as Makorin RING (Really Interesting New Gene) zinc-finger protein-155. Finally, PABP is present in neuronal granules containing proteins implicated in activity-dependent protein synthesis and RNA localization including: HuD Staufen, Zip-code-binding protein, and *Pumilio* (Barbee et al., 2006; Tiruchi-napalli et al. 2008). These results indicate that the Poly(A) SPOT-ON reduces nascent protein synthesis in both axons and cell bodies in vitro. This raises the question as to which site is relevant for the behavioral effects of PABP inhibition. As the site of delivery was the paw where axons reside, distal to cell bodies located in ganglia, one potential mechanism for the effects of the Poly(A) SPOT-ON is in axons. However, the expression of PABP in non-neuronal cells near the site of injection, including resident immune cells, underscores the ubiquitous distribution of PABP. The Poly(A) SPOT-ON is not specifically targeted to neurons and appears to be readily taken up by other cell types. Thus, the inventors cannot exclude the possibility that nonneuronal mechanisms contribute to the observed series of pharmacological effects. These experiments contribute additional understanding to the potential biological roles of PABP in nociception. Genetic loss of PAIP suggests that exaggerated PABP activity has no apparent consequence on mechanical sensitivity (Khoutorsky et al., 2013). They observed that the Poly(A) SPOT-ON elicits substantial antihyperalgesic effects on mechanical hypersensitivity. Additional experiments are required to examine the downstream targets of the Poly(A) SPOT-ON.

Sensory neurons are key mediators of nociceptive sensitization. In the peripheral nociceptive system, local protein synthesis in nociceptor terminals or their distal axons has been implicated in promoting hyperexcitability and producing pain sensitization (Obara et al., 2012). Inhibition of activity-dependent translation in axons blocks the development of persistent plasticity as measured by the presence of hyperalgesic priming. This strongly suggests that development of chronic pain requires regulated local protein synthesis. Thus, understanding basic mechanisms that drive pain sensitization is crucial for the identification of potential targets for chronic pain treatment. These data indicate that PABP inhibition can impact behavioral plasticity after injury. This contributes to prior work on the 3' end in nociceptive sensitization. For instance, local administration of an inhibitor of mRNA polyadenylation (cordyceptin) prevents hyperalgesic priming in rats 60. Additionally, the cytoplasmic polyadenylation element-binding (CPEB) RNAbinding protein contributes to nociceptor plasticity (Ferrari et al., 2013). CPEB is a target of calmodulin-activated protein kinase IIα and mediates regulated cytoplasmic polyadenylation. Taken together, these experiments support a model wherein dynamic extension of the Poly(A) tail facilitates nociceptor axonal plasticity. The inclusion of PABP in this model provides a vital link between the 3' end of mRNA and factors bound to the m7G cap via eIF4G.

In in vivo experiments, the inventors noted a decrease in pain induced by incision using mechanical stimulation, paw guarding, and facial grimace assessment. Similarly, surgically induced inflammation or capsaicin-induced inflammatory pain were decreased as a result of treatment with the Poly(A) SPOT-ON. Is the Poly(A) SPOT-ON targeting neurons or immune cells to reduce pain and inflammation? The inventors favor a scenario where the Poly(A) SPOT-ON preferentially targets nociceptors to reduce pain and inflammation. Guarding and grimace behavior is induced by ongoing nociceptor activity after injury. This ongoing activity also drives neurogenic inflammation which is a critical contributor to inflammation after injury. Neurogenic inflammation is primarily driven by CGRP release from nociceptors that trigger blood vessels to promote blood flow to the injured area 50. The capsaicin data suggest that the Poly(A) SPOT-ON blocks plasticity by a factor that has a very specific interaction with nociceptors. The combination of behavioral results using evoked and non-evoked stimuli, when taken together with the temperature-based inflammation measures, is consistent with a neuronally mediated mechanism of action for the Poly(A) SPOTON. However, these data do not exclude the possibility of a contribution from non-neuronal cell types.

To summarize, numerous mechanisms govern plasticity in nociceptors. Several of these mechanisms converge on regulated changes in Poly(A) tail length. Through the use of chemically modified RNAs, the inventors provide evidence that PABP plays an integral function in signal integration in response to inflammatory models of pain in mice. The inventors' approach suggests that targeting RNA-protein interactions may provide a new source of pharmacological agents for probing mechanism of action in vivo. This is a particularly important question given the preponderance of RNA-binding proteins encoded by the human genome whose associations with RNA lack overt function (Castello et al., 2012). The use of the SPOT-ON approach provides a novel means to interrogate this problem.

Another example of RNA-decoys targeted are those to RNA-processing factors related to cancer, specifically RBFOX, SRSF1, and PTBP133. The oligos, termed splicing factor decoys, were designed based on consensus sequences identified from the literature and confirmed by pull downs and splicing assays. As with SPOT-ONs, 2'-O-methyl substitutions were added to all of the ribose groups in all but one experiment the backbone was unmodified. To improve the potency of the oligos, tandem copies of binding elements were introduced ranging in number from 1-4. Intriguingly, increasing the number of binding sites reduced equilibrium dissociation constants implying that cooperative effects promote synergistic binding. Injection of the RBFOX oligo (8 pg) with a fully modified phosphorothioate backbone into zebrafish resulted in severe developmental defects of musculature in vivo. PTBP1 and SRSF1 decoys impaired growth of breast and glioblastoma cancer cells in vitro, respectively. Intriguingly, glioblastoma tumors seeded into the brain were noticeably smaller three weeks after injection of a single dose of an SRSF1 decoy, suggesting RBP decoys targeted to RNA processing may provide a promising new type of therapeutic for cancer (Denichenko et al., 2019).

* * * * * * * * * * * *

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

Remington's Pharmaceutical Sciences, 15$^{th}$ ed., 1035-1038 and 1570-1580, Mack Publishing Company, PA (1980).

Dagle et al., Antisense Res. Dev., 1: 11-20 (1991).

Wang, H. & Tiedge, H. Translational control at the synapse. Neurosci. Rev. J. Bringing Neurobiol. Neurol. Psychiatry 10, 456-466 (2004).

Costa-Mattioli et al., Translational control of long-lasting synaptic plasticity and memory. Neuron 61, 10-26 (2009).

Eckmann et al., Control of poly(A) tail length. Wiley Interdiscip. Rev. RNA 2, 348-361 (2011).

Sonenberg, N. & Hinnebusch, A. G. Regulation of translation initiation in eukaryotes: mechanisms and biological targets. Cell 136, 731-745 (2009).

Gallie, D. R. A tale of two termini: a functional interaction between the termini of an mRNA is a prerequisite for efficient translation initiation. Gene 216, 1-11 (1998).

Moy et al., The MNK-eIF4E signaling axis contributes to injury-induced nociceptive plasticity and the development of chronic pain. J. Neurosci. 37, 7481-7499 (2017).

Khoutorsky et al., Translational control of nociception via 4E-binding protein 1. eLife 4, //doi.org/10.7554/eLife.12002 (2015).

Melemedjian et al., IL-6- and NGF-induced rapid control of protein synthesis and nociceptive plasticity via convergent signaling to the eIF4F complex. J. Neurosci. 30, 15113-15123 (2010).

Sonenberg, N. & Hinnebusch, A. G. New modes of translational control in development, behavior, and disease. Mol. Cell 28, 721-729 (2007).

Wu et al., CPEB-mediated cytoplasmic polyadenylation and the regulation of experience-dependent translation of alpha-CaMKII mRNA at synapses. Neuron 21, 1129-1139 (1998).

Kundel et al., Cytoplasmic polyadenylation element-binding protein regulates neurotrophin-3-dependent beta-catenin mRNA translation in developing hippocampal neurons. J. Neurosci. 29, 13630-13639 (2009).

Wells et al., A role for the cytoplasmic polyadenylation element in NMDA receptor-regulated mRNA translation in neurons. J. Neurosci. 21, 9541-9548 (2001).

Gorgoni, B. & Gray, N. K. The roles of cytoplasmic poly (A)-binding proteins in regulating gene expression: a developmental perspective. Brief. Funct. Genom. Proteom. 3, 125-141 (2004).

Morales et al., Destabilization of human alphaglobin mRNA by translation anti-termination is controlled during erythroid differentiation and is paralleled by phased shortening of the poly(A) tail. J. Biol. Chem. 272, 6607-6613 (1997).

Couttet et al., Messenger RNA deadenylylation precedes decapping in mammalian cells. Proc. Natl. Acad. Sci. USA 94, 5628-5633 (1997).

Burgess, H. M. & Gray, N. K. mRNA-specific regulation of translation by poly (A)-binding proteins. Biochem. Soc. Trans. 38, 1517-1522 (2010).

Ray et al., A compendium of RNA-binding motifs for decoding gene regulation. Nature 499, 172-177 (2013).

Dias, N. & Stein, C. A. Antisense oligonucleotides: basic concepts and mechanisms. Mol. Cancer Ther. 1, 347-355 (2002).

Kole et al., RNA therapeutics: beyond RNA interference and antisense oligonucleotides. Nat. Rev. Drug. Discov. 11, 125-140 (2012).

Campbell et al., Oligodeoxynucleoside phosphorothioate stability in subcellular extracts, culture media, sera and cerebrospinal fluid. J. Biochem. Biophys. Methods 20, 259-267 (1990).

Gerhold et al., The star-nosed mole reveals clues to the molecular basis of mammalian touch. PLoS ONE 8, e55001 (2013).

Campbell et al., Cooperativity in RNA-protein interactions: global analysis of RNA binding specificity. Cell Rep. 1, 570-581 (2012).

Campbell et al., A protein-RNA specificity code enables targeted activation of an endogenous human transcript. Nat. Struct. Mol. Biol. 21, 732-738 (2014).

Weidmann et al., *Drosophila* nanos acts as a molecular clamp that modulates the RNA-binding and repression activities of *pumilio*. eLife 5, //doi.org/10.7554/eLife.17096 (2016).

Kini et al., Cytoplasmic poly(A) binding protein-1 binds to genomically encoded sequences within mammalian mRNAs. RNA 22, 61-74 (2016).

Kahvejian et al., The mRNA closed-loop model: the function of PABP and PABP-interacting proteins in mRNA translation. Cold Spring Harb. Symp. Quant. Biol. 66, 293-300 (2001).

Mangus et al., Poly(A)-binding proteins: multifunctional scaffolds for the post-transcriptional control of gene expression. Genome Biol. 4, 223 (2003).

Gorgoni et al., Poly(A)-binding proteins are functionally distinct and have essential roles during vertebrate development. Proc. Natl. Acad. Sci. USA 108, 7844-7849 (2011).

Sachs, A. in Translational Control of Gene Expression (ed. Mathews, M. B.) Ch. 10 (Cold Spring Harbor Laboratory Press, Cold Spring Harbor, N.Y., 2000).

Hernandez, F. J. et al. Degradation of nuclease-stabilized RNA oligonucleotides in *Mycoplasma*-contaminated cell culture media. Nucleic Acid Ther. 22, 58-68 (2012).

Ciafre et al., Stability and functional effectiveness of phosphorothioate modified duplex DNA and synthetic "minigenes". Nucleic Acids Res. 23, 4134-4142 (1995).

Deo et al., Recognition of polyadenylate RNA by the poly(A)-binding protein. Cell 98, 835-845 (1999).

Svitkin, Y. V. & Sonenberg, N. An efficient system for cap- and poly(A)-dependent translation in vitro. Methods Mol. Biol. 257, 155-170 (2004).

Schmidt et al., SUnSET, a nonradioactive method to monitor protein synthesis. Nat. Methods 6, 275-277 (2009).

Nathans, D. Puromycin inhibition of protein synthesis: incorporation of puromycin into peptide chains. Proc. Natl. Acad. Sci. USA 51, 585-592 (1964).

David et al., RNA binding targets aminoacyl-tRNA synthetases to translating ribosomes. J. Biol. Chem. 286, 20688-20700 (2011).

David et al., Nuclear translation visualized by ribosome-bound nascent chain puromycylation. J. Cell. Biol. 197, 45-57 (2012).

Willett et al., Translation initiation factors and active sites of protein synthesis co-localize at the leading edge of migrating fibroblasts. Biochem. J. 438, 217-227 (2011).

Graber et al., Reactivation of stalled polyribosomes in synaptic plasticity. Proc. Natl. Acad. Sci. USA 110, 16205-16210 (2013).

Gallie, D. R. The cap and poly(A) tail function synergistically to regulate mRNA translational efficiency. Genes Dev. 5, 2108-2116 (1991).

Tarun, S. Z. Jr & Sachs, A. B. Association of the yeast poly(A) tail binding protein with translation initiation factor eIF-4G. EMBO J. 15, 7168-7177 (1996).

Le et al., Translation initiation factors eIF-iso4G and eIF-4B interact with the poly(A)-binding protein and increase its RNA binding activity. J. Biol. Chem. 272, 16247-16255 (1997).

Imataka et al., A newly identified N-terminal amino acid sequence of human eIF4G binds poly(A)-binding protein and functions in poly(A)-dependent translation. EMBO J. 17, 7480-7489 (1998).

Price, T. J. & Geranton, S. M. Translating nociceptor sensitivity: the role of axonal protein synthesis in nociceptor physiology. Eur. J. Neurosci. 29, 2253-2263 (2009).

Koenig et al., Cryptic peripheral ribosomal domains distributed intermittently along mammalian myelinated axons. J. Neurosci. 20, 8390-8400 (2000).

Reichling, D. B. & Levine, J. D. Critical role of nociceptor plasticity in chronic pain. Trends Neurosci. 32, 611-618 (2009).

Banik et al., Increased nerve growth factor after rat plantar incision contributes to guarding behavior and heat hyperalgesia. Pain 117, 68-76 (2005).

Spofford, C. M. & Brennan, T. J. Gene expression in skin, muscle, and dorsal root ganglion after plantar incision in the rat. Anesthesiology 117, 161-172 (2012).

Sanchez et al., Use of a portable thermal imaging unit as a rapid, quantitative method of evaluating inflammation and experimental arthritis. J. Pharmacol. Toxicol. Methods 57, 169-175 (2008).

Richardson et al., Cellular mechanisms of neurogenic inflammation. J. Pharmacol. Exp. Ther. 302, 839-845 (2002).

Li, Z. & Rana, T. M. Therapeutic targeting of microRNAs: current status and future challenges. Nat. Rev. Drug. Discov. 13, 622-638 (2014).

Castello et al., Insights into RNA biology from an atlas of mammalian mRNA-binding proteins. Cell 149, 1393-1406 (2012).

Muddashetty et al., Poly(A)-binding protein is associated with neuronal BC1 and BC200 ribonucleoprotein particles. J. Mol. Biol. 321, 433-445 (2002).

Zhang et al., QNQKE targeting motif for the SMN-Gemin multiprotein complexin neurons. J. Neurosci. Res. 85, 2657-2667 (2007).

Miroci et al., Makorin ring zinc finger protein 1 (MKRN1), a novel poly(A)-binding protein-interacting protein, stimulates translation in nerve cells. J. Biol. Chem. 287, 1322-1334 (2012).

Barbee et al., Staufen- and FMRP-containing neuronal RNPs are structurally and functionally related to somatic P bodies. Neuron 52, 997-1009 (2006).

Tiruchinapalli et al., Activity-dependent expression of RNA binding protein HuD and its association with mRNAs in neurons. RNA Biol. 5, 157-168 (2008).

Khoutorsky et al., Control of synaptic plasticity and memory via suppression of poly(A)-binding protein. Neuron 78, 298-311 (2013).

Obara et al., Axonal protein synthesis: a potential target for pain relief? Curr. Opin. Pharmacol. 12, 42-48 (2012).

Ferrari et al., Peripheral administration of translation inhibitors reverses increased hyperalgesia in a model of chronic pain in the rat. J. Pain 14, 731-738 (2013).

Bogen et al., Generation of a pain memory in the primary afferent nociceptor triggered by PKCepsilon activation of CPEB. J. Neurosci. 32, 2018-2026 (2012).

Lou et al., Integrated analysis of RNA-binding protein complexes using in vitro selection and high-throughput sequencing and sequence specificity landscapes (SE-QRS). Methods 118-119, 171-181 (2017).

Campbell et al., Identification of a conserved interface between PUF and CPEB proteins. J. Biol. Chem. 287, 18854-18862 (2012).

Bolte, S. & Cordelieres, F. P. A guided tour into subcellular colocalization analysis in light microscopy. J. Microsc. 224, 213-232 (2006).

Aley et al., Chronic hypersensitivity for inflammatory nociceptor sensitization mediated by the epsilon isozyme of protein kinase C. J. Neurosci. 20, 4680-4685 (2000).

Chaplan et al., Quantitative assessment of tactile allodynia in the rat paw. J. Neurosci. Methods 53, 55-63 (1994).

Banik et al., Strain and sex influence on pain sensitivity after plantar incision in the mouse. Anesthesiology 105, 1246-1253 (2006).

Langford et al., Coding of facial expressions of pain in the laboratory mouse. Nat. Methods 7, 447-449 (2010).

Feltri et al., P0-Cre transgenic mice for inactivation of adhesion molecules in Schwann cells. Ann. NY Acad. Sci. 883, 116-123 (1999).

Liu et al., Cell-specific translational profiling in acute kidney injury. J. Clin. Invest. 124, 1242-1254 (2014).

Denichenko et al., Nat Commun 10,1590, doi:10.1038/s41467-019-09523-0 (2019).

---

What is claimed is:

1. A compound comprising a chemically-stabilized 2'O-Methyl modified RNA substrate that hybridizes to an RNA binding protein (RNA-BP) with high specificity in vitro and alters RNA processing, alters RNA stability and/or impairs nascent translation in RNA-BP-dependent mechanism in cells, wherein (a) said chemically-stabilized RNA substrate is represented by the formula:

$$[mA]*[mA][mA][mA][mA][mA][mA][mA][mA][mA]$$
$$[mA]*[mA] \qquad \text{(SEQ ID NO: 1)}$$

wherein each base is bracketed, * denotes a phosphorothioate bond, and m denotes 2'O-Methyl modification; and/or (b) further comprising a targeting agent linked to said chemically-stabilized RNA.

2. The compound of claim 1, wherein said RNA-BP is poly-A binding protein (PABP), eukaryotic translation initiation factor 4E (eIF4E), HuD or ELAV Like RNA Binding Protein 4 (Elavl4), HuR or ELAV Like RNA Binding Protein 1 (Elavl1), Cytoplasmic polyadenylation element binding protein (CPEB), or Fragile X mental retardation protein (FMRP).

3. The compound of claim 1, wherein said compound is 11-15 bases in length.

4. The compound of claim 1, wherein said chemically-stabilized RNA substrate is represented by the formula:

$$[mA]*[mA][mA][mA][mA][mA][mA][mA][mA][mA]$$
$$[mA]*[mA] \qquad \text{(SEQ ID NO: 1)}$$

wherein each base is bracketed, * denotes a phosphorothioate bond, and m denotes 2'O-Methyl modification.

5. The compound of claim 1, further comprising a targeting agent linked to said chemically-stabilized RNA.

6. The compound of claim 1, wherein said RNA-BP alters RNA processing.

7. The compound of claim 1, wherein said RNA-BP alters RNA stability and impairs nascent translation.

8. A method of altering RNA processing, altering RNA stability and/or impairing nascent translation in a subject comprising administering to said subject a compound of claim 1.

9. The method of claim 8, wherein administering comprises oral, intravenous, intra-arterial administration or subcutaneous administration.

10. The method of claim 8, comprising administering said compound a second time.

11. The method of claim 8, wherein said subject suffers from pain and said administering treats said pain.

12. The method of claim 11, wherein administering comprises administering local or regional to a site of pain.

13. The method of claim 11, further comprising administering to said subject one or more of an NSAID, an opiate, or a steroid.

14. The method of claim 11, wherein pain is neuropathic pain.

15. The method of claim 14, wherein neuropathic pain is peripheral neuropathic pain.

16. The method of claim 11, wherein pain is inflammatory pain.

17. The method of claim 16, wherein inflammatory pain is nociceptive pain.

18. The method of claim 11, wherein said subject suffers from chronic pain.

19. The method of claim 11, wherein said subject suffers from severe/acute pain.

20. The compound of claim 1, wherein said RNA-BP alters RNA processing and RNA stability and impairs nascent translation.

21. The method of claim 9, wherein the administering is by a transdermal patch.

22. The method of claim 12, wherein the administering is by a transdermal patch.

* * * * *